US012296178B2

(12) United States Patent
Perryman et al.

(10) Patent No.: US 12,296,178 B2
(45) Date of Patent: *May 13, 2025

(54) STIMULATION WITH ELECTRODE ARRAYS

(71) Applicant: CURONIX LLC, Pompano Beach, FL (US)

(72) Inventors: Laura Tyler Perryman, Miami, FL (US); Chad David Andresen, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,268

(22) Filed: Dec. 21, 2023

(65) Prior Publication Data

US 2024/0123237 A1     Apr. 18, 2024

Related U.S. Application Data

(60) Continuation of application No. 17/409,373, filed on Aug. 23, 2021, now Pat. No. 11,857,796, which is a
(Continued)

(51) Int. Cl.
*A61N 1/372* (2006.01)
*A61N 1/05* (2006.01)
*A61N 1/378* (2006.01)

(52) U.S. Cl.
CPC ........... *A61N 1/37217* (2013.01); *A61N 1/05* (2013.01); *A61N 1/37247* (2013.01); *A61N 1/37264* (2013.01); *A61N 1/3787* (2013.01)

(58) Field of Classification Search
CPC .. A61N 1/37217; A61N 1/05; A61N 1/37247; A61N 1/37264; A61N 1/3787
See application file for complete search history.

(56) References Cited

U.S. PATENT DOCUMENTS 4,793,353 A    12/1988  Borkan
6,473,653 B1   10/2002  Schallhorn et al.
(Continued)

FOREIGN PATENT DOCUMENTS

WO    2012103519 A2    8/2012
WO    2012138782 A1    10/2012
(Continued)

*Primary Examiner* — Mark W. Bockelman
(74) *Attorney, Agent, or Firm* — Maschoff Brennan

(57) ABSTRACT

A device for implantation in a patient may include an electrode arrays configured to apply at least one electrical pulse to an excitable tissue, the electrode array including at least one electrode; connector contacts, each integrally wired to a particular electrode array, each configured to drive the at least one electrode of the particular electrode array integrally wired thereto with the at least one electrical pulse; a first antenna configured to: receive, from a second antenna and through electrical radiative coupling, an input signal containing electrical energy, the second antenna located outside the patient's body; and one or more circuits electrically connected to the first antenna and the connector contacts, the circuits configured to: create the one or more electrical pulses suitable for stimulation of the excitable tissue by using the electrical energy contained in the input signal; and supply the one or more electrical pulses to the connector contacts.

20 Claims, 27 Drawing Sheets

Related U.S. Application Data continuation of application No. 16/273,752, filed on Feb. 12, 2019, now Pat. No. 11,097,111, which is a division of application No. 14/722,224, filed on May 27, 2015, now Pat. No. 10,265,530.

(60) Provisional application No. 62/004,284, filed on May 29, 2014.

(56) References Cited

U.S. PATENT DOCUMENTS

| | | | |
|---|---|---|---|
| 6,645,178 B1 | 11/2003 | Junker et al. | |
| 6,909,917 B2 | 6/2005 | Woods et al. | |
| 7,072,719 B2 | 7/2006 | Vinup et al. | |
| 7,127,298 B1 | 10/2006 | He et al. | |
| 7,590,454 B2 | 9/2009 | Garabedian et al. | |
| 8,543,222 B1 | 9/2013 | Sochor | |
| 8,655,453 B2 | 2/2014 | Werder et al. | |
| 8,849,412 B2 | 9/2014 | Perryman et al. | |
| 9,199,089 B2 | 12/2015 | Perryman et al. | |
| 9,220,897 B2 | 12/2015 | Perryman et al. | |
| 9,242,103 B2 | 1/2016 | Perryman et al. | |
| 9,409,030 B2 | 8/2016 | Perryman et al. | |
| 9,566,449 B2 | 2/2017 | Perryman et al. | |
| 9,757,571 B2 | 9/2017 | Perryman et al. | |
| 9,789,314 B2 | 10/2017 | Perryman et al. | |
| 9,925,384 B2 | 3/2018 | Perryman et al. | |
| 9,974,965 B2 | 5/2018 | Perryman et al. | |
| 10,238,874 B2 | 3/2019 | Perryman et al. | |
| 10,265,530 B1 | 4/2019 | Perryman et al. | |
| 10,315,039 B2 | 6/2019 | Perryman et al. | |
| 10,420,947 B2 | 9/2019 | Perryman et al. | |
| 10,471,262 B2 | 11/2019 | Perryman et al. | |
| 11,097,111 B1 | 8/2021 | Perryman et al. | |
| 2018/0264277 A1 | 9/2018 | Perryman et al. | |
| 2019/0247660 A1 | 8/2019 | Perryman et al. | |
| 2019/0381327 A1 | 12/2019 | Perryman et al. | |
| 2020/0016415 A1 | 1/2020 | Perryman et al. | |

FOREIGN PATENT DOCUMENTS

| | | |
|---|---|---|
| WO | 2013019757 A1 | 2/2013 |
| WO | 2013025632 A1 | 2/2013 |
| WO | 2013040549 A1 | 3/2013 |
| WO | 2014089299 A1 | 6/2014 |

STIMULATION WITH ELECTRODE ARRAYS

CROSS REFERENCE TO RELATED APPLICATIONS

This application is a continuation of U.S. application Ser. No. 17/409,373, filed Aug. 23, 2021, which is a continuation of U.S. application Ser. No. 16/273,752, filed Feb. 12, 2019, which is a divisional of U.S. application Ser. No. 14/722,224, filed May 27, 2015, which claims the benefit of U.S. provisional Patent Application 62/004,284, filed May 29, 2014. The subject matter of each of the prior applications are incorporated by reference in their entirety.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

DETAILED DESCRIPTION

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a wireless stimulation device may be used to send electrical energy to targeted nerve tissue by using remote radio frequency (RF) energy with neither cables nor inductive coupling to power the passive implanted wireless stimulation device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable, wireless stimulation device with one or more electrodes and an enclosure that houses one or more conductive antennas (for example, dipole or patch antennas), and internal circuitry for frequency waveform and electrical energy rectification. The system may further comprise an external controller and antenna for sending radio frequency or microwave energy from an external source to the implantable device with neither cables nor inductive coupling to provide power.

In various embodiments, the implantable device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil. Further descriptions of exemplary wireless systems for providing neural stimulation to a patient can be found in commonly-assigned, co-pending published PCT applications PCT/US2012/23029 filed Jan. 27, 2012, PCT/US2012/32200 filed Apr. 11, 2012, PCT/US2012/48903, filed Jan. 28, 2012, PCT/US2012/50633, filed Aug. 12, 2012, PCT/US2012/55746, filed Sep. 15, 2012 and PCT/US2013/073326, filed Dec. 5, 2013, the complete disclosures of which have been previously incorporated by reference.

Figure 1:
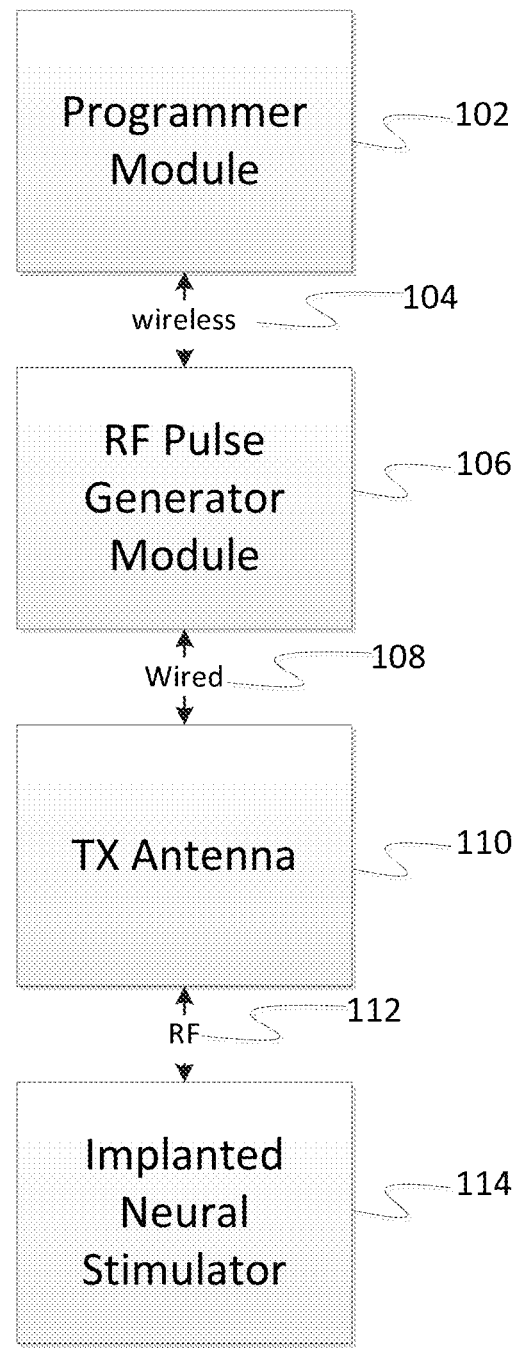
FIG. 1 depicts a high-level diagram of an example of a wireless stimulation system.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implantable wireless stimulation device 114. The programmer module 102 may be a computer device, such as a smart phone, running a software application that supports a wireless connection 114, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted neural stimulator module 114. The TX antenna 110 communicates with the implanted neural stimulator module 114 through an RF interface. For instance, the TX antenna 110 radiates an RF transmission signal that is modulated and encoded by the RF pulse generator module 110. The implanted wireless stimulation device of module 114 contains one or more antennas, such as dipole antenna (s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted stimulation module 114. This input signal contains energy and may contain information encoding stimulus waveforms to be applied at the electrodes of the implanted stimulation module 114. In some implementations, the power level of this input signal directly determines an applied amplitude (for example, power, current, or voltage) of the one or more electrical pulses created using the electrical energy contained in the input signal. Within the implanted wireless stimulation device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulation device module 114. In either event, receiver circuit(s) internal to the wireless stimulation device 114 (or connector device 1400 shown in FIG. 14A) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulation device 114 based on RF signals received from the implanted wireless stimulation device module 114. A feedback detection algorithm implemented by the RF pulse generator module 106 can monitor data sent wirelessly from the implanted wireless stimulation device module 114, including information about the energy that the implanted wireless stimulation device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulation device 114 are monitored and used to determine the appropriate level of neural stimulation current for maintaining effective neuronal activation, or, in some cases, the patient can manually adjust the output signals in an open loop control method.

Figure 2:
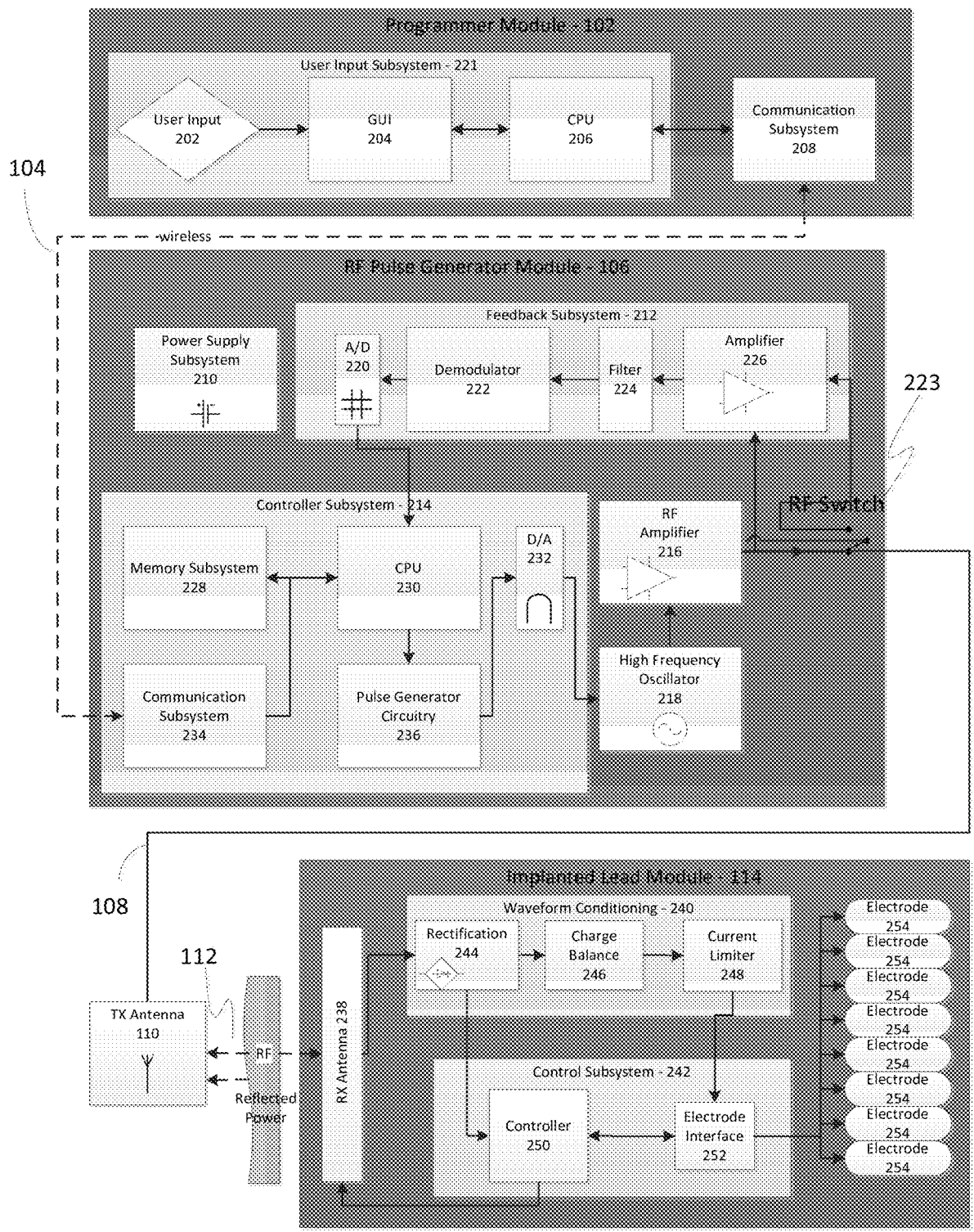
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 20 mA |
| Pulse Frequency: | 0 to 10000 Hz |
| Pulse Width: | 0 to 2 ms |

The RF pulse generator module 114 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulation device 114 may include both power and parameter-setting attributes in regards to stimulus waveform, amplitude, pulse width, and frequency. The RF pulse generator module 106 can also function as a wireless receiving unit that receives feedback signals from the implanted wireless stimulation device 114. To that end, the RF pulse generator module 106 may contain microelectronics or other circuitry to handle the generation of the signals transmitted to the device 114 as well as handle feedback signals, such as those from the device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receive (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulation device module 114 to send instructions about the various operations of the wireless stimulation device module 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same device to power the wireless stimulation device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulation device 114), the RF switch 223 is set to send the forward power signal to feedback subsystem. During the off-cycle time (when an RF signal is not being transmitted to the wireless stimulation device module 114), the RF switch 223 can change to a receiving mode in which the reflected RF energy and/or RF signals from the wireless stimulation device module 114 are received to be analyzed in the feedback subsystem 212.

The feedback subsystem 212 of the RF pulse generator module 106 may include reception circuitry to receive and extract telemetry or other feedback signals from the wireless stimulation device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulation device 114 may transmit informational signals, such as a telemetry signal, through the antenna 238 to communicate with the RF pulse generator module 106 during its receive cycle. For example, the telemetry signal from the wireless stimulation device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulation device 114.

A telemetry signal from the implanted wireless stimulation device module 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulation device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulation device 114 delivered the specified stimuli to tissue. For example, if the wireless stimulation device reports a lower current than was specified, the power level from the RF pulse generator module 106 can be increased so that the implanted wireless stimulation device 114 will have more available power for stimulation. The implanted wireless stimulation device 114 can generate telemetry data in real time, for example, at a rate of 8 Kbits per second. All feedback data received from the implanted module 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulation device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulation device module 114 to be converted into electrical pulses applied to the electrodes 254 through electrode interface 252. In some implementations, the implanted wireless stimulation device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulation device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulation device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulation device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulation device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative—voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulation device module 114 may create a drive-waveform envelope that follows the envelope of the RF pulse received by the receiving dipole antenna(s) 238. In this case, the RF pulse generator module 106 can directly control the envelope of the drive waveform within the wireless stimulation device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulation device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulation device 114, such as controller 250. In the case of onboard control, the amplitude and timing may be specified or modified by data commands delivered from the pulse generator module 106.

Figure 3:
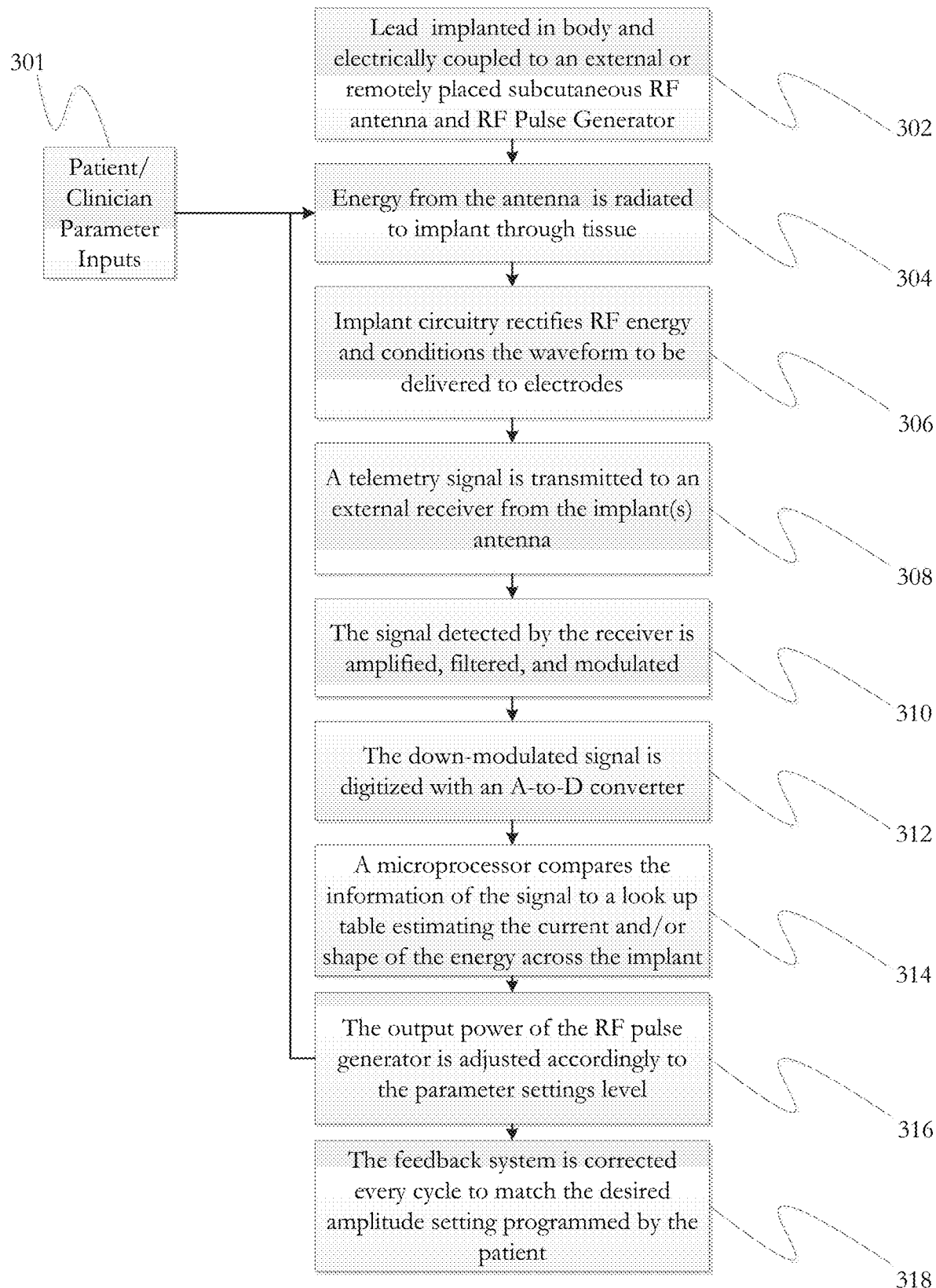
FIG. 3 is a flowchart showing an example of the operation of the wireless stimulation system.

FIG. 3 is a flowchart showing an example of an operation of the wireless stimulation system. In block 302, the wireless stimulation device 114 is implanted in proximity to nerve bundles and is coupled to the electric field produced by the TX antenna 110. That is, the pulse generator module 106 and the TX antenna 110 are positioned in such a way (for example, in proximity to the patient) that the TX antenna 110 is electrically radiatively coupled with the implanted RX antenna 238 of the wireless stimulation device 114. In certain implementations, both the antenna 110 and the RF pulse generator 106 are located subcutaneously. In other implementations, the antenna 110 and the RF pulse generator 106 are located external to the patient's body. In this case, the TX antenna 110 may be coupled directly to the patient's skin.

Energy from the RF pulse generator is radiated to the implanted wireless stimulation device 114 from the antenna 110 through tissue, as shown in block 304. The energy radiated may be controlled by the Patient/Clinician Parameter inputs in block 301. In some instances, the parameter settings can be adjusted in an open loop fashion by the patient or clinician, who would adjust the parameter inputs in block 301 to the system.

The implanted wireless stimulation device 114 uses the received energy to generate electrical pulses to be applied to the neural tissue through the electrodes 238. For instance, the wireless stimulation device 114 may contain circuitry that rectifies the received RF energy and conditions the waveform to charge balance the energy delivered to the electrodes to stimulate the targeted nerves or tissues, as shown in block 306. The implanted wireless stimulation device 114 communicates with the pulse generator 106 by using antenna 238 to send a telemetry signal, as shown in block 308. The telemetry signal may contain information about parameters of the electrical pulses applied to the electrodes, such as the impedance of the electrodes, whether the safe current limit has been reached, or the amplitude of the current that is presented to the tissue from the electrodes.

In block 310, the RF pulse generator 106 detects amplifies, filters and modulates the received telemetry signal using amplifier 226, filter 224, and demodulator 222, respectively. The A/D converter 230 then digitizes the resulting analog signal, as shown in 312. The digital telemetry signal is routed to CPU 230, which determines whether the parameters of the signal sent to the wireless stimulation device 114 need to be adjusted based on the digital telemetry signal. For instance, in block 314, the CPU 230 compares the information of the digital signal to a look-up table, which may indicate an appropriate change in stimulation parameters. The indicated change may be, for example, a change in the current level of the pulses applied to the electrodes. As a result, the CPU may change the output power of the signal sent to wireless stimulation device 114 so as to adjust the current applied by the electrodes 254, as shown in block 316.

Thus, for instance, the CPU 230 may adjust parameters of the signal sent to the wireless stimulation device 114 every cycle to match the desired current amplitude setting programmed by the patient, as shown in block 318. The status of the stimulator system may be sampled in real time at a rate of 8 Kbits per second of telemetry data. All feedback data received from the wireless stimulation device 114 can be maintained against time and sampled per minute to be stored for download or upload to a remote monitoring system accessible by the health care professional for trending and statistical correlations in block 318. If operated in an open loop fashion, the stimulator system operation may be reduced to just the functional elements shown in blocks 302, 304, 306, and 308, and the patient uses their judgment to adjust parameter settings rather than the closed looped feedback from the implanted device.

Figure 4:
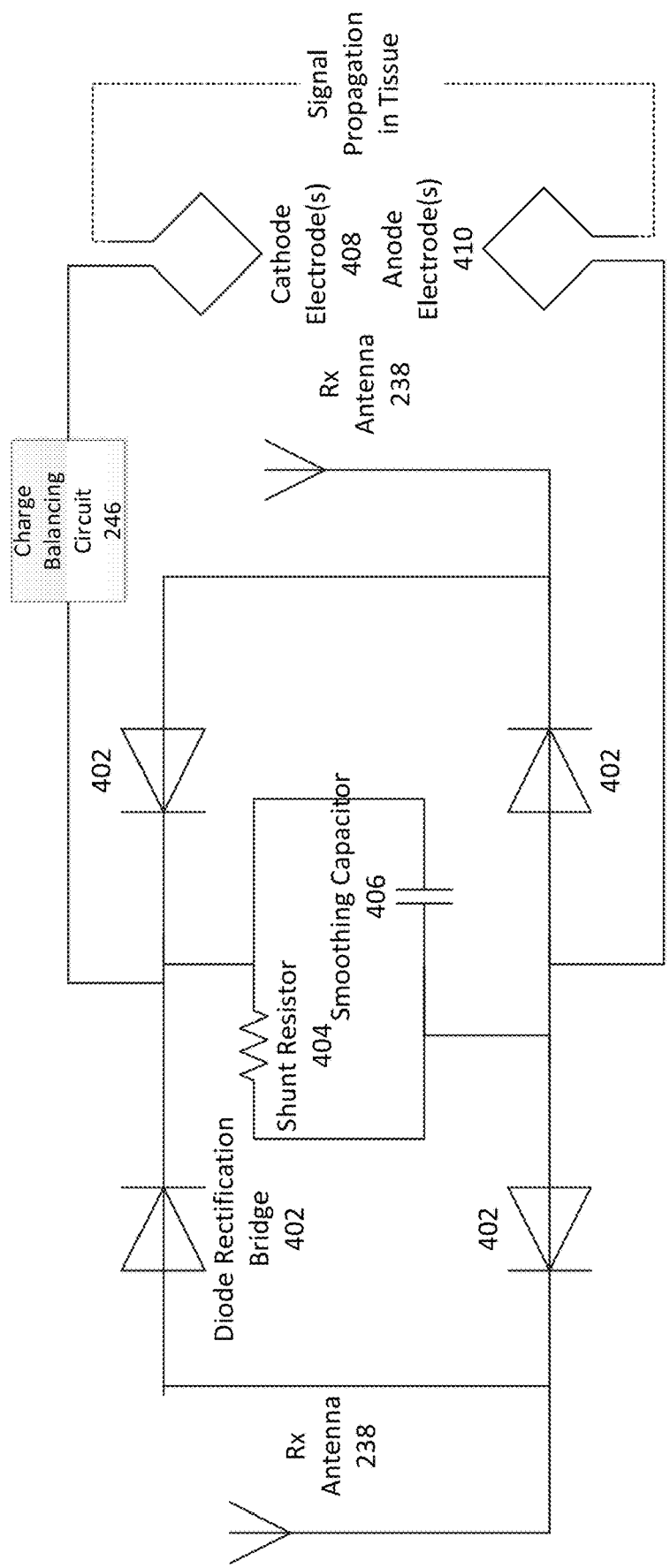
FIG. 4 is a circuit diagram showing an example of a wireless stimulation device.

FIG. 4 is a circuit diagram showing an example of a wireless neural stimulator, such as wireless stimulation device 114. This example contains paired electrodes, comprising cathode electrode(s) 408 and anode electrode(s) 410, as shown. When energized, the charged electrodes create a volume conduction field of current density within the tissue. In this implementation, the wireless energy is received through a dipole antenna(s) 238. At least four diodes are connected together to form a full wave bridge rectifier 402 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may result in a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 includes two branches of diode pairs connecting an anode-to-anode and then cathode to cathode. The electrodes 408 and 410 are connected to the output of the charge balancing circuit 246.

Figure 5:
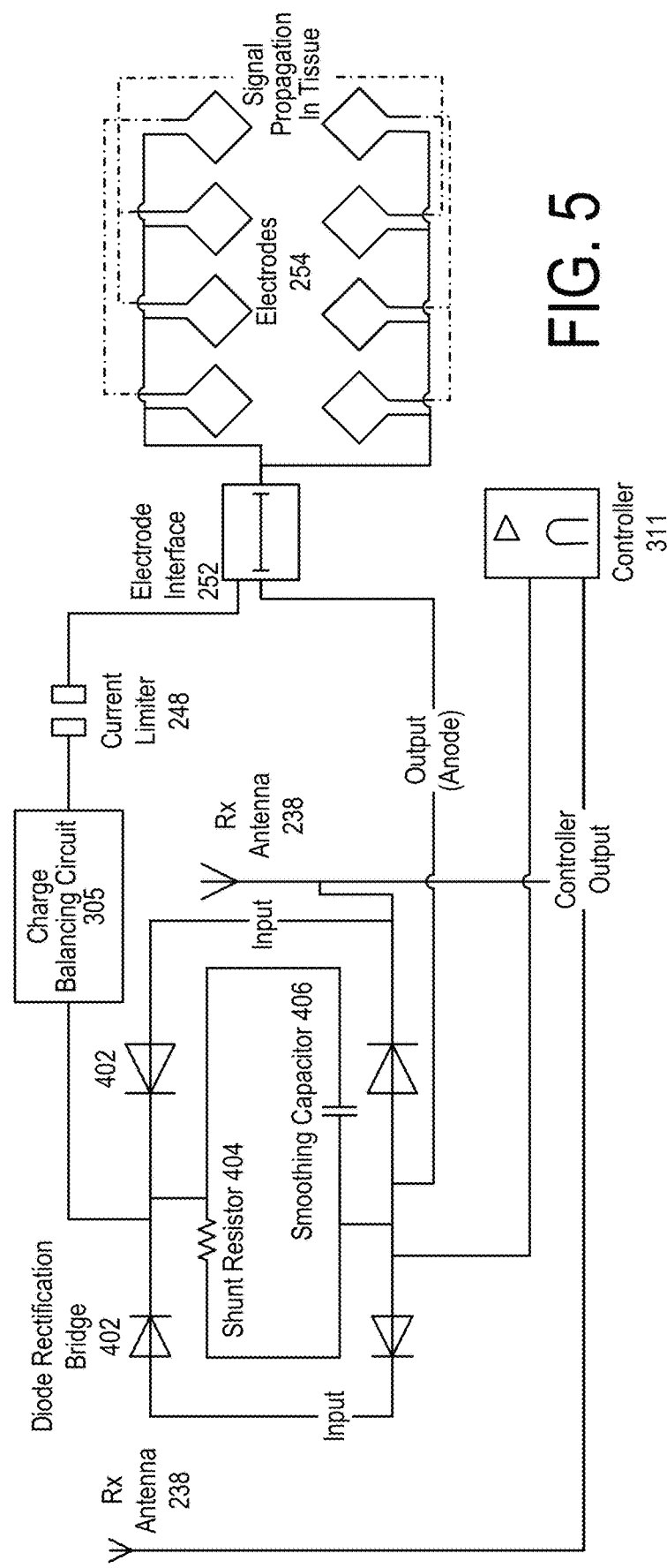
FIG. 5 is a circuit diagram of another example of a wireless stimulation device.

FIG. 5 is a circuit diagram of another example of a wireless stimulation device 114. The example shown in FIG. 5 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may result in a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 may include two branches of diode pairs connecting an anode-to-anode and then cathode to cathode. The electrode polarity outputs, both cathode 408 and anode 410 are connected to the outputs formed by the bridge connection. Charge balancing circuitry 246 and current limiting circuitry 248 are placed in series with the outputs.

Figure 6:
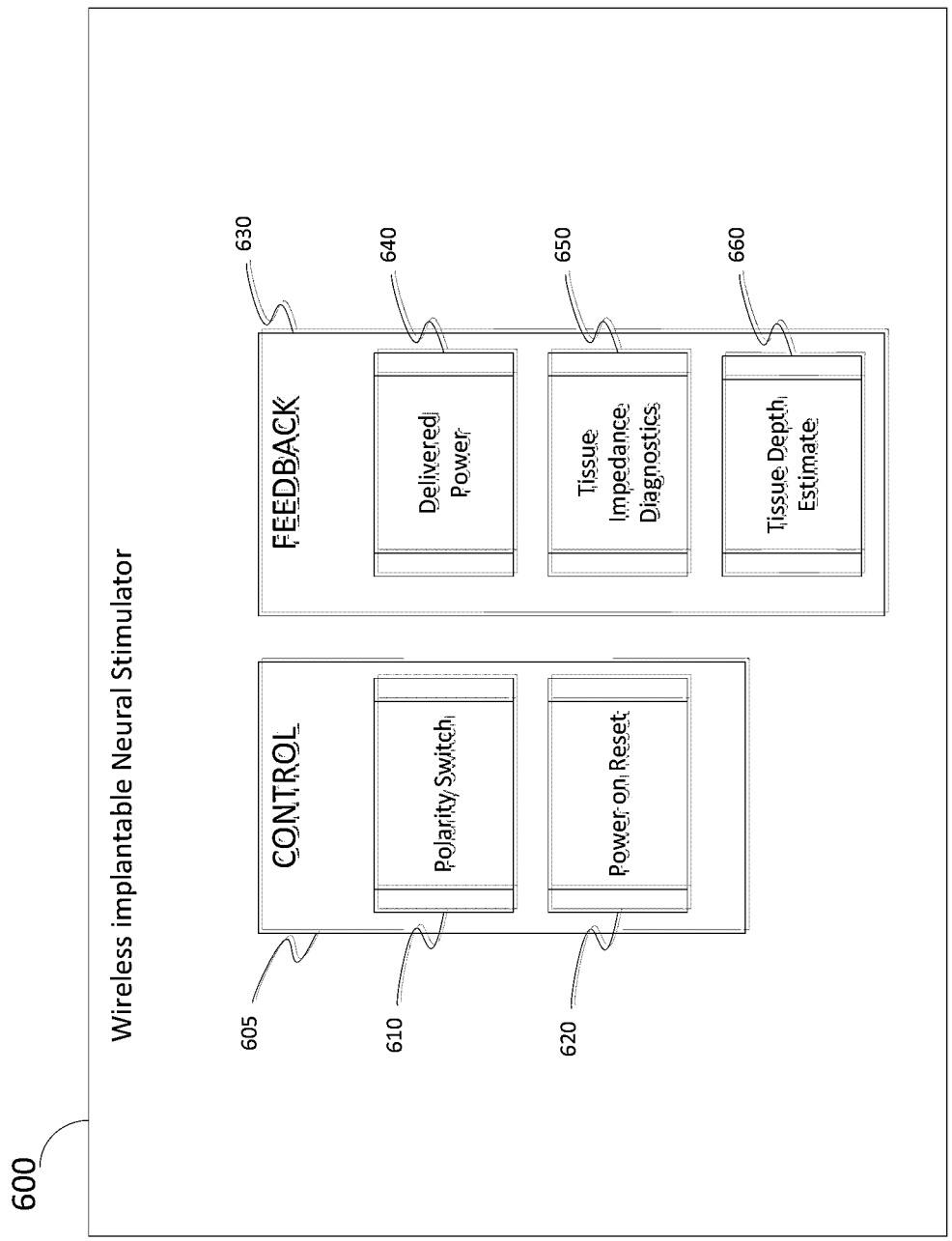
FIG. 6 is a block diagram showing an example of control and feedback functions of a wireless stimulation device.

FIG. 6 is a block diagram showing an example of control functions 605 and feedback functions 630 of an implantable wireless stimulation device 600, such as the ones described above or further below. An example implementation may be a wireless stimulation device module 114, as discussed above in association with FIG. 2. Control functions 605 include functions 610 for polarity switching of the electrodes and functions 620 for power-on reset.

Polarity switching functions 610 may employ, for example, a polarity routing switch network to assign polarities to electrodes 254. The assignment of polarity to an electrode may, for instance, be one of: a cathode (negative polarity), an anode (positive polarity), or a neutral (off) polarity. The polarity assignment information for each of the electrodes 254 may be contained in the input signal received by implantable wireless stimulation device 600 through Rx antenna 238 from RF pulse generator module 106. Because a programmer module 102 may control RF pulse generator module 106, the polarity of electrodes 254 may be controlled remotely by a programmer through programmer module 102, as shown in FIG. 2.

Power-on reset functions 620 may reset the polarity assignment of each electrode immediately on each power-on event. As will be described in further detail below, this reset operation may cause RF pulse generator module 106 to transmit the polarity assignment information to the implantable wireless stimulation device 600. Once the polarity assignment information is received by the implantable wireless stimulation device 600, the polarity assignment information may be stored in a register file, or other short-term memory component. Thereafter the polarity assignment information may be used to configure the polarity assignment of each electrode. If the polarity assignment information transmitted in response to the reset encodes the same polarity state as before the power-on event, then the polarity state of each electrode can be maintained before and after each power-on event.

Feedback functions 630 include functions 640 for monitoring delivered power to electrodes 254 and functions 650 for making impedance diagnosis of electrodes 254. For example, delivered power functions 640 may provide data encoding the amount of power being delivered from electrodes 254 to the excitable tissue and tissue impedance diagnostic functions 650 may provide data encoding the diagnostic information of tissue impedance. The tissue impedance is the electrical impedance of the tissue as seen between negative and positive electrodes when a stimulation current is being released between negative and positive electrodes.

Feedback functions 630 may additionally include tissue depth estimate functions 660 to provide data indicating the overall tissue depth that the input radio frequency (RF) signal from the pulse generator module, such as, for example, RF pulse generator module 106, has penetrated before reaching the implanted antenna, such as, for example, RX antenna 238, within the wireless implantable neural stimulator 600, such as, for example, implanted wireless stimulation device 114. For instance, the tissue depth estimate may be provided by comparing the power of the received input signal to the power of the RF pulse transmitted by the RF pulse generator 106. The ratio of the power of the received input signal to the power of the RF pulse transmitted by the RF pulse generator 106 may indicate an attenuation caused by wave propagation through the tissue. For example, the second harmonic described below may be received by the RF pulse generator 106 and used with the power of the input signal sent by the RF pulse generator to determine the tissue depth. The attenuation may be used to infer the overall depth of implantable wireless stimulation device 600 underneath the skin.

The data from blocks 640, 650, and 660 may be transmitted, for example, through Tx antenna 110 to an implantable RF pulse generator 106, as illustrated in FIGS. 1 and 2.

As discussed above in association with FIGS. 1, 2, 4, and 5, an implantable wireless stimulation device 600 may utilize rectification circuitry to convert the input signal (e.g., having a carrier frequency within a range from about 300 MHz to about 8 GHz) to a direct current (DC) power to drive the electrodes 254. Some implementations may provide the capability to regulate the DC power remotely. Some implementations may further provide different amounts of power to different electrodes, as discussed in further detail below.

Figure 7:
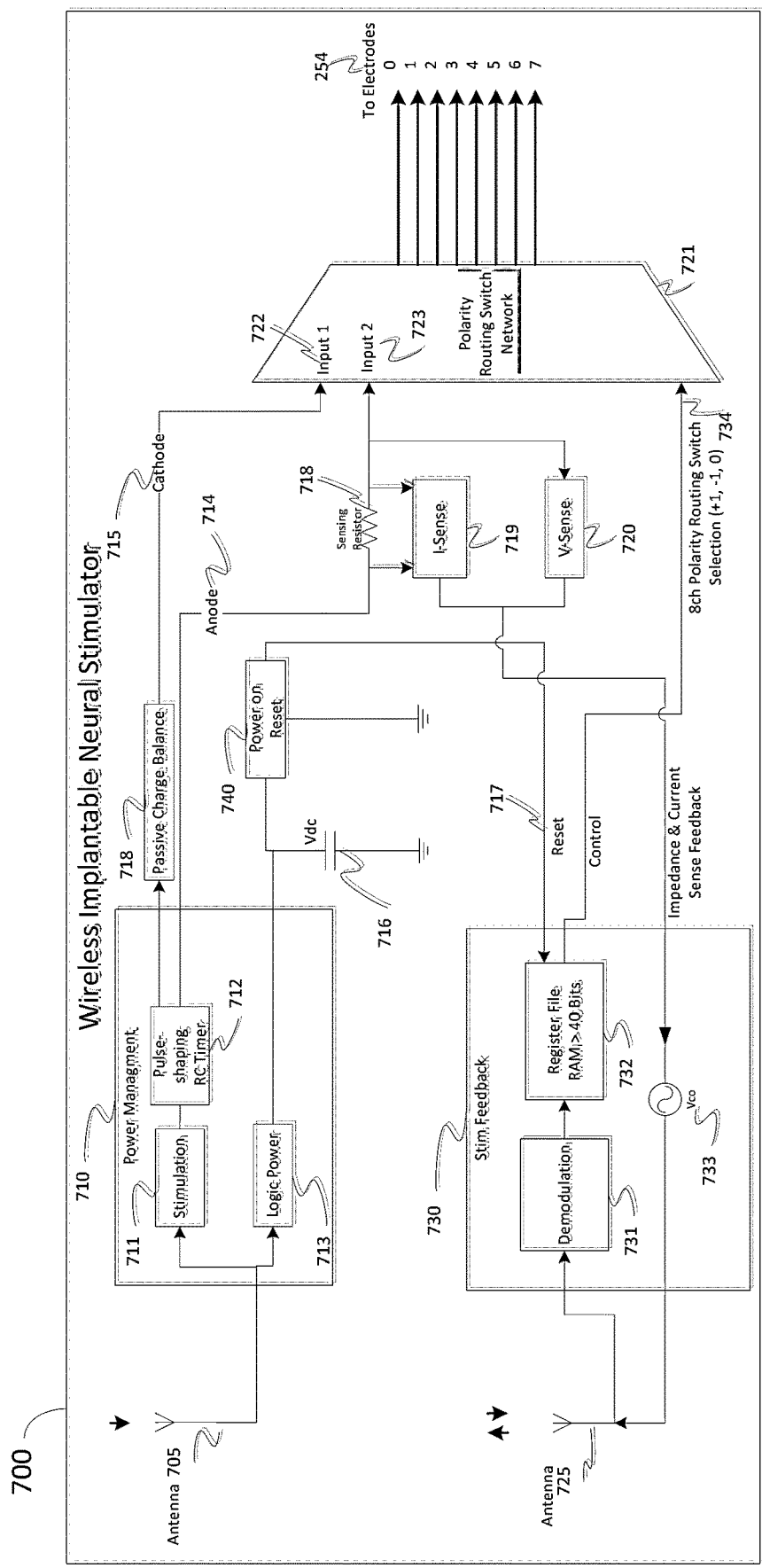
FIG. 7 is a schematic showing an example of a wireless stimulation device with components to implement control and feedback functions.

FIG. 7 is a schematic showing an example of an implantable wireless stimulation device 700 with components to implement control and feedback functions as discussed above in association with FIG. 6. An RX antenna 705 receives the input signal. The RX antenna 705 may be embedded as a dipole, microstrip, folded dipole or other antenna configuration other than a coiled configuration, as described above. The input signal has a carrier frequency in the GHz range and contains electrical energy for powering the wireless implantable neural stimulator 700 and for providing stimulation pulses to electrodes 254. Once received by the antenna 705, the input signal is routed to power management circuitry 710. Power management circuitry 710 is configured to rectify the input signal and convert it to a DC power source. For example, the power management circuitry 710 may include a diode rectification bridge such as the diode rectification bridge 402 illustrated in FIG. 4. The DC power source provides power to stimulation circuitry 711 and logic power circuitry 713. The rectification may utilize one or more full wave diode bridge rectifiers within the power management circuitry 710. In one implementation, a resistor can be placed across the output nodes of the bridge rectifier to discharge the electrodes to the ground of the bridge anode, as illustrated by the shunt register 404 in FIG. 7.

Figure 8:
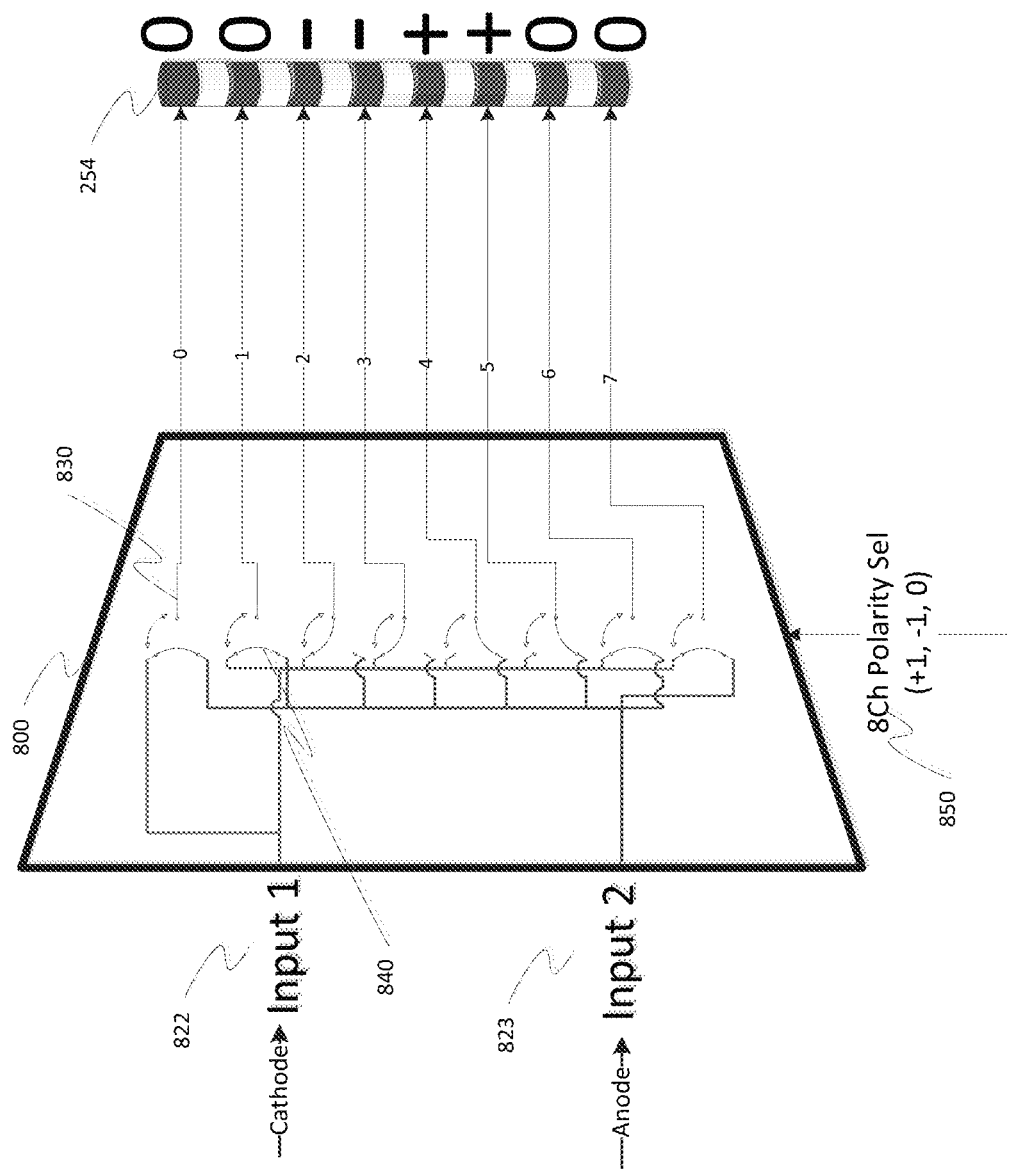
FIG. 8 is a schematic of an example of a polarity routing switch network.

Turning momentarily to FIG. 8, a schematic of an example of a polarity routing switch network 800 is shown. As discussed above, the cathodic (−) energy and the anodic energy are received at input 1 (block 722) and input 2 (block 723), respectively. Polarity routing switch network 800 has one of its outputs coupled to an electrode of electrodes 254 which can include as few as two electrodes, or as many as sixteen electrodes. Eight electrodes are shown in this implementation as an example.

Polarity routing switch network 800 is configured to either individually connect each output to one of input 1 or input 2, or disconnect the output from either of the inputs. This selects the polarity for each individual electrode of electrodes 254 as one of: neutral (off), cathode (negative), or anode (positive). Each output is coupled to a corresponding three-state switch 830 for setting the connection state of the output. Each three-state switch is controlled by one or more of the bits from the selection input 850. In some implementations, selection input 850 may allocate more than one bits to each three-state switch. For example, two bits may encode the three-state information. Thus, the state of each output of polarity routing switch device 800 can be controlled by information encoding the bits stored in the register 732, which may be set by polarity assignment information received from the remote RF pulse generator module 106, as described further below.

Returning to FIG. 7, power and impedance sensing circuitry may be used to determine the power delivered to the tissue and the impedance of the tissue. For example, a sensing resistor 718 may be placed in serial connection with the anodic branch 714. Current sensing circuit 719 senses the current across the resistor 718 and voltage sensing circuit 720 senses the voltage across the resistor. The measured current and voltage may correspond to the actual current and voltage applied by the electrodes to the tissue.

As described below, the measured current and voltage may be provided as feedback information to RF pulse generator module 106. The power delivered to the tissue may be determined by integrating the product of the measured current and voltage over the duration of the waveform being delivered to electrodes 254. Similarly, the impedance of the tissue may be determined based on the measured voltage being applied to the electrodes and the current being applied to the tissue. Alternative circuitry (not shown) may also be used in lieu of the sensing resistor 718, depending on implementation of the feature and whether both impedance and power feedback are measured individually, or combined.

The measurements from the current sensing circuitry 719 and the voltage sensing circuitry 720 may be routed to a voltage controlled oscillator (VCO) 733 or equivalent circuitry capable of converting from an analog signal source to a carrier signal for modulation. VCO 733 can generate a digital signal with a carrier frequency. The carrier frequency may vary based on analog measurements such as, for example, a voltage, a differential of a voltage and a power, etc. VCO 733 may also use amplitude modulation or phase shift keying to modulate the feedback information at the carrier frequency. The VCO or the equivalent circuit may be generally referred to as an analog controlled carrier modulator. The modulator may transmit information encoding the sensed current or voltage back to RF pulse generator 106.

Antenna 725 may transmit the modulated signal, for example, in the GHz frequency range, back to the RF pulse generator module 106. In some embodiments, antennas 705 and 725 may be the same physical antenna. In other embodiments, antennas 705 and 725 may be separate physical antennas. In the embodiments of separate antennas, antenna 725 may operate at a resonance frequency that is higher than the resonance frequency of antenna 705 to send stimulation feedback to RF pulse generator module 106. In some embodiments, antenna 725 may also operate at the higher resonance frequency to receive data encoding the polarity assignment information from RF pulse generator module 106.

Antenna 725 may include a telemetry antenna 725 which may route received data, such as polarity assignment information, to the stimulation feedback circuit 730. The encoded polarity assignment information may be on a band in the GHz range. The received data may be demodulated by demodulation circuitry 731 and then stored in the register file 732. The register file 732 may be a volatile memory. Register file 732 may be an 8-channel memory bank that can store, for example, several bits of data for each channel to be assigned a polarity. Some embodiments may have no register file, while some embodiments may have a register file up to 64 bits in size. The information encoded by these bits may be sent as the polarity selection signal to polarity routing switch network 721, as indicated by arrow 734. The bits may encode the polarity assignment for each output of the polarity routing switch network as one of: + (positive), − (negative), or 0 (neutral). Each output connects to one electrode and the channel setting determines whether the electrode will be set as an anode (positive), cathode (negative), or off (neutral).

Returning to power management circuitry 710, in some embodiments, approximately 90% of the energy received is routed to the stimulation circuitry 711 and less than 10% of the energy received is routed to the logic power circuitry 713. Logic power circuitry 713 may power the control components for polarity and telemetry. In some implementations, the power circuitry 713, however, does not provide the actual power to the electrodes for stimulating the tissues. In certain embodiments, the energy leaving the logic power circuitry 713 is sent to a capacitor circuit 716 to store a certain amount of readily available energy. The voltage of the stored charge in the capacitor circuit 716 may be denoted as Vdc. Subsequently, this stored energy is used to power a power-on reset circuit 716 configured to send a reset signal on a power-on event. If the wireless implantable neural stimulator 700 loses power for a certain period of time, for example, in the range from about 1 millisecond to over 10 milliseconds, the contents in the register file 732 and polarity setting on polarity routing switch network 721 may be zeroed. The implantable wireless stimulation device 700 may lose power, for example, when it becomes less aligned with RF pulse generator module 106. Using this stored energy, power-on reset circuit 740 may provide a reset signal as indicated by arrow 717. This reset signal may cause stimulation feedback circuit 730 to notify RF pulse generator module 106 of the loss of power. For example, stimulation feedback circuit 730 may transmit a telemetry feedback signal to RF pulse generator module 106 as a status notification of the power outage. This telemetry feedback signal may be transmitted in response to the reset signal and immediately after power is back on wireless stimulation device 700. RF pulse generator module 106 may then transmit one or more telemetry packets to implantable wireless stimulation device. The telemetry packets contain polarity assignment information, which may be saved to register file 732 and may be sent to polarity routing switch network 721. Thus, polarity assignment information in register file 732 may be recovered from telemetry packets transmitted by RF pulse generator module 106 and the polarity assignment for each output of polarity routing switch network 721 may be updated accordingly based on the polarity assignment information.

The telemetry antenna 725 may transmit the telemetry feedback signal back to RF pulse generator module 106 at a frequency higher than the characteristic frequency of an RX antenna 705. In one implementation, the telemetry antenna 725 can have a heightened resonance frequency that is the second harmonic of the characteristic frequency of RX antenna 705. For example, the second harmonic may be utilized to transmit power feedback information regarding an estimate of the amount of power being received by the electrodes. The feedback information may then be used by the RF pulse generator in determining any adjustment of the power level to be transmitted by the RF pulse generator 106. In a similar manner, the second harmonic transmission can be used to detect the tissue depth. The second harmonic transmission can be detected by an external antenna, for example, on RF pulse generator module 106 that is tuned to the second harmonic. As a general matter, power management circuitry 710 may contain rectifying circuits that are non-linear device capable of generating harmonic energies from input signal. Harvesting such harmonic energy for transmitting telemetry feedback signal could improve the efficiency of implantable wireless stimulation device 700.

Figure 9A:
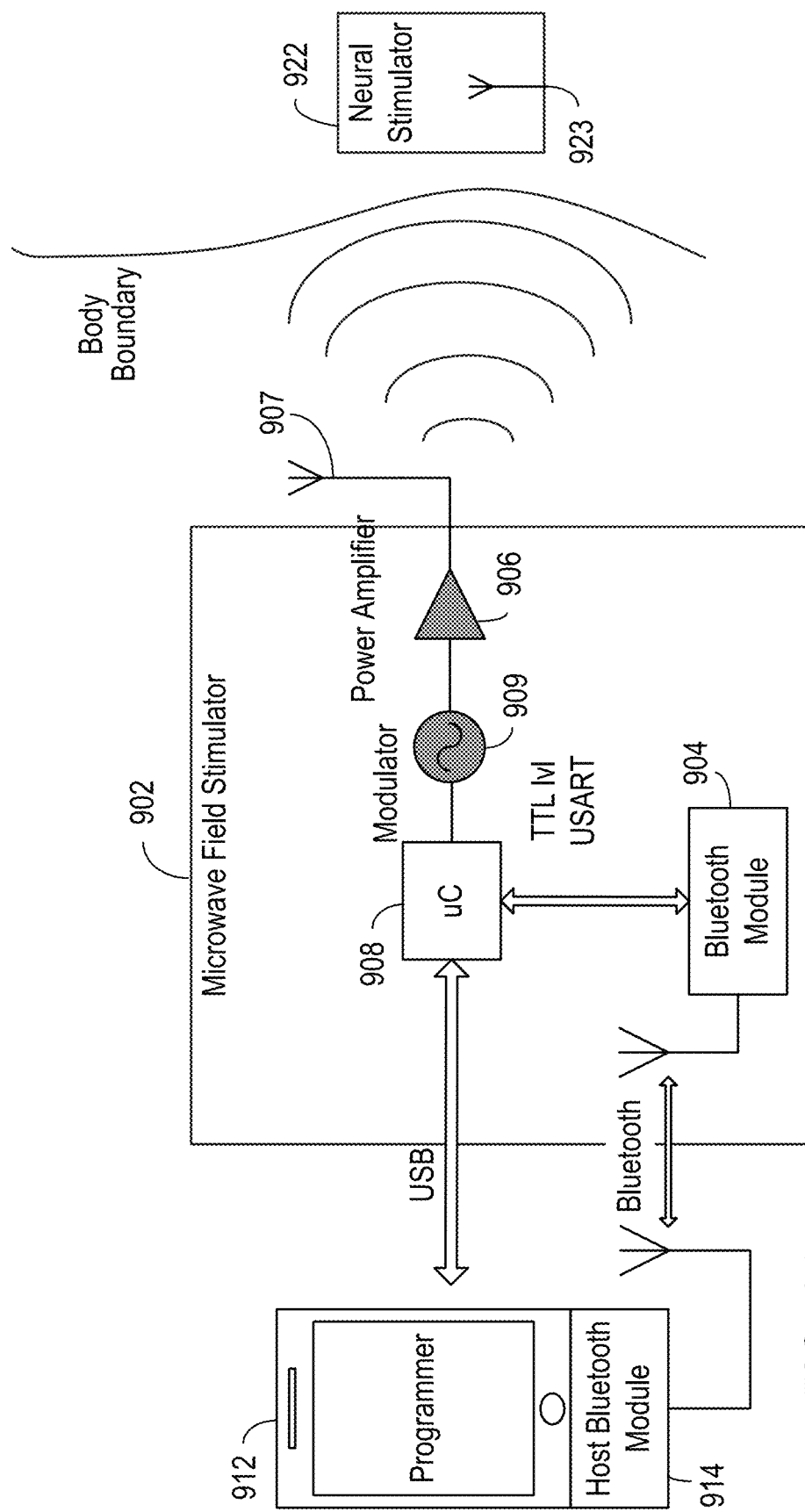
FIG. 9A is a diagram of an example microwave field stimulator (MFS) operating along with a wireless stimulation device.

FIG. 9A is a diagram of an example implementation of a microwave field stimulator (MFS) 902 as part of a stimulation system utilizing an implantable wireless stimulation device 922. In this example, the MFS 902 is external to a patient's body and may be placed within in close proximity, for example, within 3 feet, to an implantable wireless stimulation device 922. The RF pulse generator module 106 may be one example implementation of MFS 902. MFS 902 may be generally known as a controller module. The implantable wireless stimulation device 922 is a passive device. The implantable wireless stimulation device 922 does not have its own independent power source, rather it receives power for its operation from transmission signals emitted from a TX antenna powered by the MFS 902, as discussed above.

In certain embodiments, the MFS 902 may communicate with a programmer 912. The programmer 912 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 904, which communicates with the host bluetooth module 914 within the programmer 912.

The MFS 902 may additionally communicate with wireless stimulation device 922 by transmitting a transmission signal through a Tx antenna 907 coupled to an amplifier 906. The transmission signal may propagate through skin and underlying tissues to arrive at the Rx antenna 923 of the wireless stimulation device 922. In some implementations, the wireless stimulation device 922 may transmit a telemetry feedback signal back to microwave field stimulator 902.

The microwave field stimulator 902 may include a microcontroller 908 configured to manage the communication with a programmer 912 and generate an output signal. The output signal may be used by the modulator 909 to modulate a RF carrier signal. The frequency of the carrier signal may be in the microwave range, for example, from about 300 MHz to about 8 GHz, preferably from about 800 MHz to 1.3 GHz. The modulated RF carrier signal may be amplified by an amplifier 906 to provide the transmission signal for transmission to the wireless stimulation device 922 through a TX antenna 907.

Figure 9B:
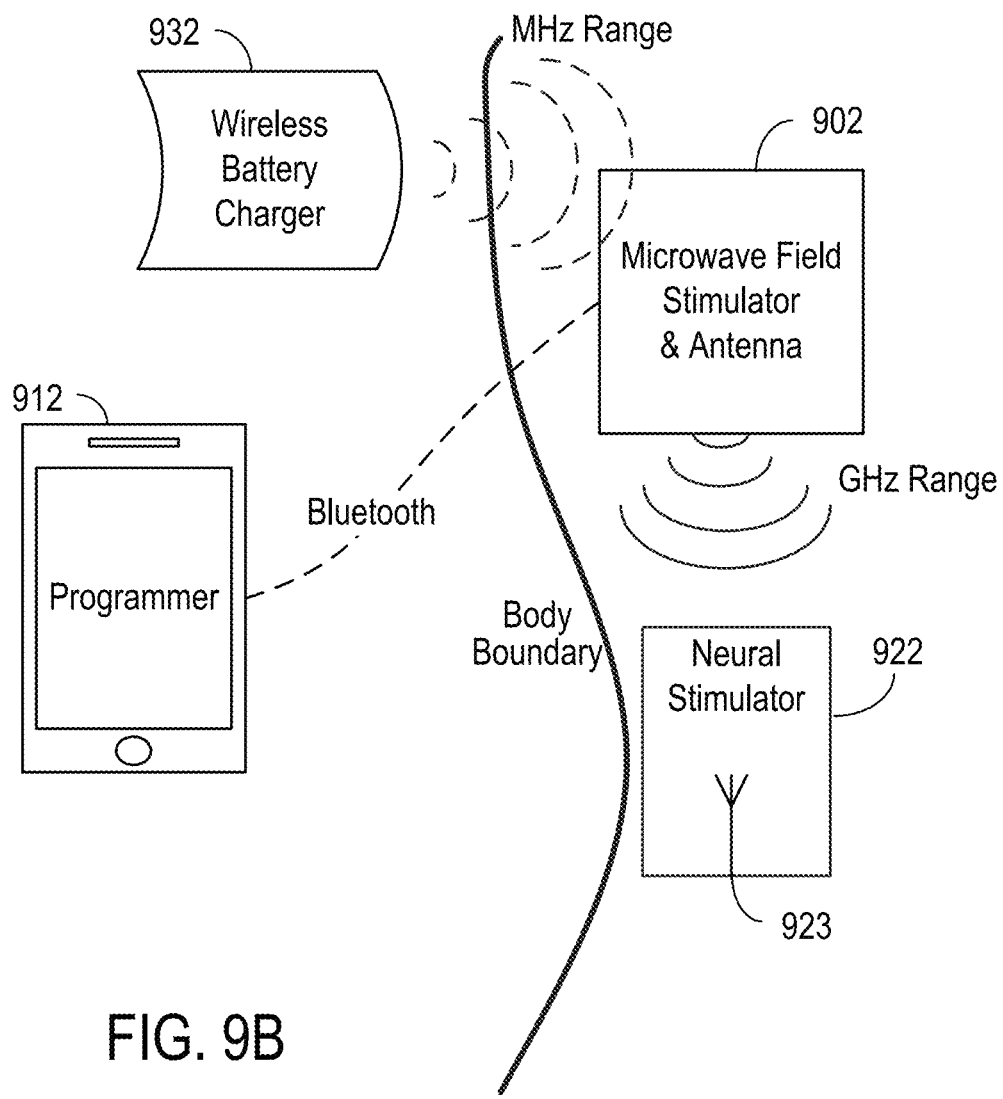
FIG. 9B is a diagram of another example MFS operating along with a wireless stimulation device.

FIG. 9B is a diagram of another example of an implementation of a microwave field stimulator 902 as part of a stimulation system utilizing a wireless stimulation device 922. In this example, the microwave field stimulator 902 may be embedded in the body of the patient, for example, subcutaneously. The embedded microwave field stimulator 902 may receive power from a detached, remote wireless battery charger 932.

The power from the wireless battery charger 932 to the embedded microwave field stimulator 902 may be transmitted at a frequency in the MHz or GHz range. The microwave field stimulator 902 shall be embedded subcutaneously at a very shallow depth (e.g., less than 1 cm), and alternative coupling methods may be used to transfer energy from wireless battery charger 932 to the embedded MFS 902 in the most efficient manner as is well known in the art.

In some embodiments, the microwave field stimulator 902 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the microwave field stimulator 902 shall transmit power and parameter signals to a passive Tx antenna also embedded subcutaneously, which shall be coupled to the RX antenna within the wireless stimulation device 922. The power required in this embodiment is substantially lower since the TX antenna and the RX antenna are already in body tissue and there is no requirement to transmit the signal through the skin.

Figure 10:
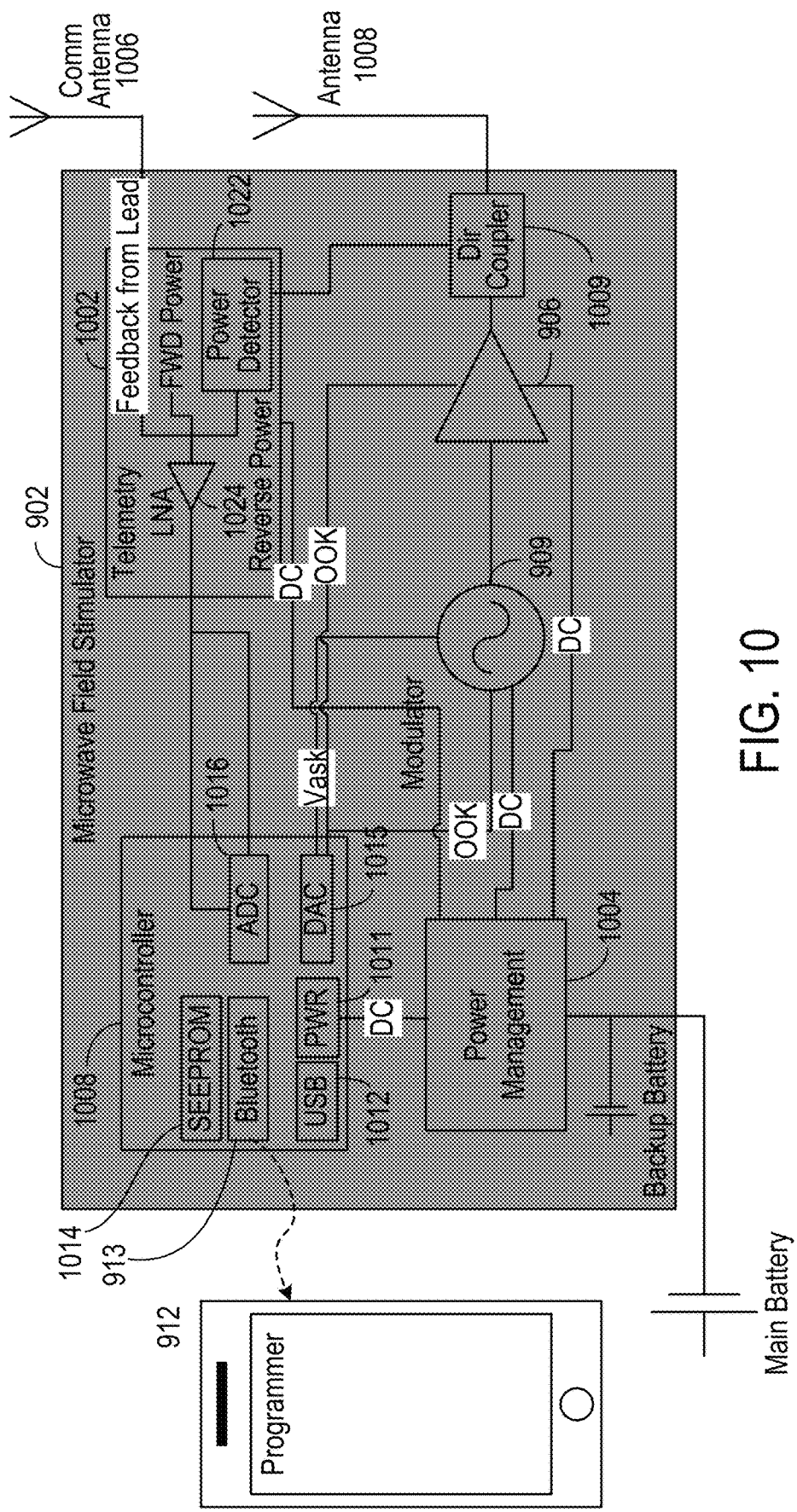
FIG. 10 is a detailed diagram of an example MFS.

FIG. 10 is a detailed diagram of an example microwave field stimulator 902. A microwave field stimulator 902 may include a microcontroller 908, a telemetry feedback module 1002, and a power management module 1004. The microwave field stimulator 902 has a two-way communication schema with a programmer 912, as well as with a communication or telemetry antenna 1006. The microwave field stimulator 902 sends output power and data signals through a TX antenna 1008.

The microcontroller 908 may include a storage device 1014, a bluetooth interface 1013, a USB interface 1012, a power interface 1011, an analog-to-digital converter (ADC) 1016, and a digital to analog converter (DAC) 1015. Implementations of a storage device 1014 may include non-volatile memory, such as, for example, static electrically erasable programmable read-only memory (SEEPROM) or NAND flash memory. A storage device 1014 may store waveform parameter information for the microcontroller 908 to synthesize the output signal used by modulator 909. The stimulation waveform may include multiple pulses. The waveform parameter information may include the shape, duration, amplitude of each pulse, as well as pulse repetition frequency. A storage device 1014 may additionally store polarity assignment information for each electrode of the wireless stimulation device 922. The Bluetooth interface 1013 and USB interface 1012 respectively interact with either the bluetooth module 1004 or the USB module to communicate with the programmer 912.

The communication antenna 1006 and a TX antenna 1008 may, for example, be configured in a variety of sizes and form factors, including, but not limited to a patch antenna, a slot antenna, or a dipole antenna. The TX antenna 1008 may be adapted to transmit a transmission signal, in addition to power, to the implantable, passive neural stimulator 922. As discussed above, an output signal generated by the microcontroller 908 may be used by the modulator 909 to provide the instructions for creation of a modulated RF carrier signal. The RF carrier signal may be amplified by amplifier 906 to generate the transmission signal. A directional coupler 1009 may be utilized to provide two-way coupling so that both the forward power of the transmission signal flow transmitted by the TX antenna 1008 and the reverse power of the reflected transmission may be picked up by power detector 1022 of telemetry feedback module 1002. In some implementations, a separate communication antenna 1006 may function as the receive antenna for receiving telemetry feedback signal from the wireless stimulation device 922. In some configurations, the communication antenna may operate at a higher frequency band than the TX antenna 1008. For example, the communication antenna 1006 may have a characteristic frequency that is a second harmonic of the characteristic frequency of TX antenna 1008, as discussed above.

In some embodiments, the microwave field stimulator 902 may additionally include a telemetry feedback module 902. In some implementations, the telemetry feedback module 1002 may be coupled directly to communication antenna 1006 to receive telemetry feedback signals. The power detector 1022 may provide a reading of both the forward power of the transmission signal and a reverse power of a portion of the transmission signal that is reflected during transmission. The telemetry signal, forward power reading, and reverse power reading may be amplified by low noise amplifier (LNA) 1024 for further processing. For example, the telemetry module 902 may be configured to process the telemetry feedback signal by demodulating the telemetry feedback signal to extract the encoded information. Such encoded information may include, for example, a status of the wireless stimulation device 922 and one or more electrical parameters associated with a particular channel (electrode) of the wireless stimulation device 922. Based on the decoded information, the telemetry feedback module 1002 may be used to calculate a desired operational characteristic for the wireless stimulation device 922.

Some embodiments of the MFS 902 may further include a power management module 1004. A power management module 1004 may manage various power sources for the MFS 902. Example power sources include, but are not limited to, lithium-ion or lithium polymer batteries. The power management module 1004 may provide several operational modes to save battery power. Example operation modes may include, but are not limited to, a regular mode, a low power mode, a sleep mode, a deep sleep/hibernate mode, and an off mode. The regular mode provides regulation of the transmission of transmission signals and stimulus to the wireless stimulation device 922. In regular mode, the telemetry feedback signal is received and processed to monitor the stimuli as normal. Low-power mode also provides regulation of the transmission of transmission signals and stimulus to the electrodes of the wireless stimulation device. However, under this mode, the telemetry feedback signal may be ignored. More specifically, the telemetry feedback signal encoding the stimulus power may be ignored, thereby saving MFS 902 overall power consumption. Under sleep mode, the transceiver and amplifier 906 are turned off, while the microcontroller is kept on with the last saved state in its memory. Under the deep sleep/hibernate mode, the transceiver and amplifier 906 are turned off, while the microcontroller is in power down mode, but power regulators are on. Under the off mode, all transceiver, microcontroller and regulators are turned off achieving zero quiescent power.

Figure 11:
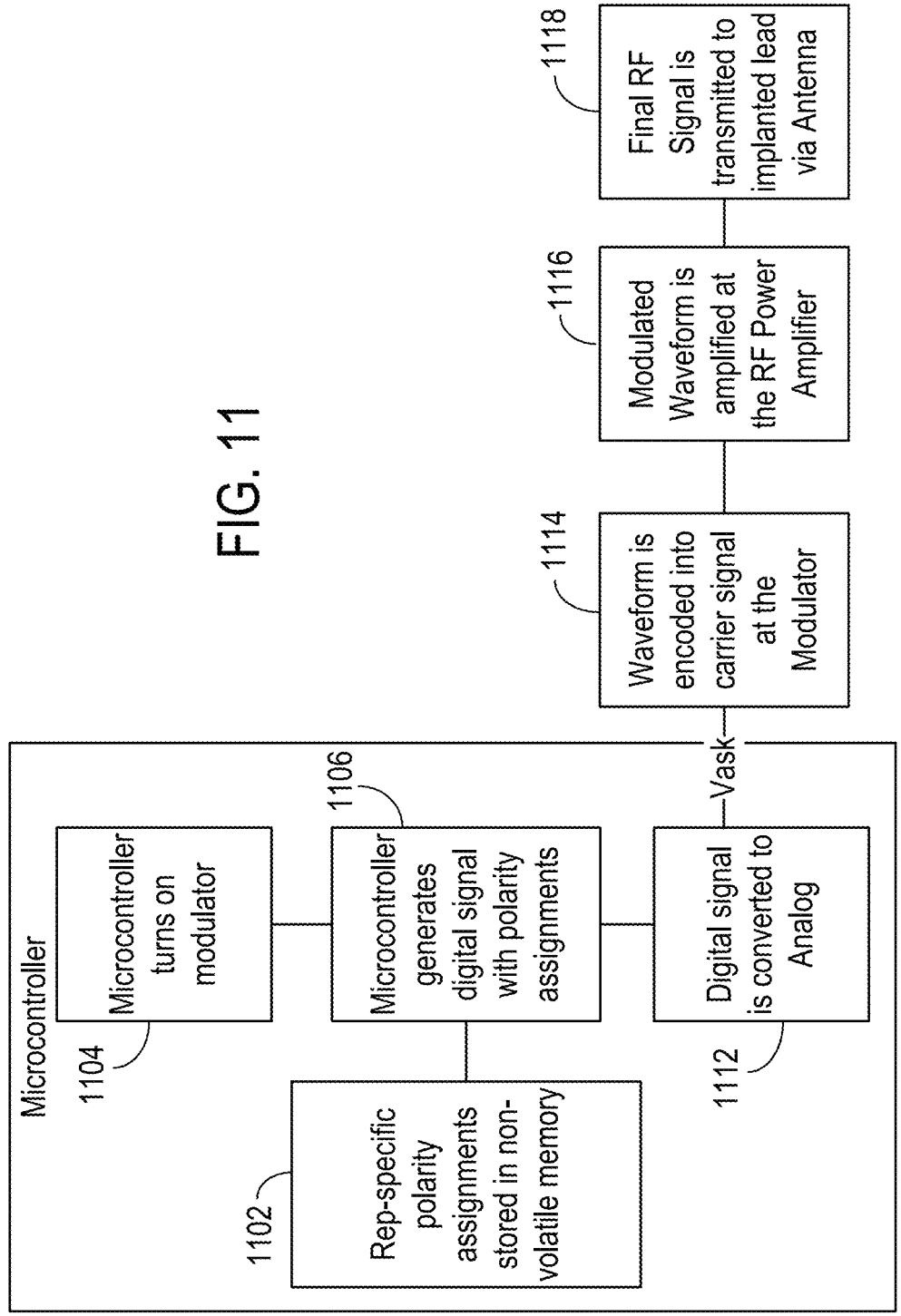
FIG. 11 is a flowchart showing an example process in which the MFS transmits polarity setting information to the wireless stimulation device.

FIG. 11 is a flowchart showing an example process in which the microwave field stimulator 902 transmits polarity setting information to the wireless stimulation device 922. Polarity assignment information is stored in a non-volatile memory 1102 within the microcontroller 908 of the MFS 902. The polarity assignment information may be representative-specific and may be chosen to meet the specific need of a particular patient. Based on the polarity assignment information chosen for a particular patient, the microcontroller 908 executes a specific routine for assigning polarity to each electrode of the electrode array. The particular patient has a wireless stimulation device as described above.

In some implementations, the polarity assignment procedure includes sending a signal to the wireless stimulation device with an initial power-on portion followed by a configuration portion that encodes the polarity assignments. The power-on portion may, for example, simply include the RF carrier signal. The initial power-on portion has a duration that is sufficient to power-on the wireless stimulation device and allow the device to reset into a configuration mode. Once in the configuration mode, the device reads the encoded information in the configuration portion and sets the polarity of the electrodes as indicated by the encoded information.

Thus, in some implementations, the microcontroller 908 turns on the modulator 909 so that the unmodulated RF carrier is sent to the wireless stimulation device 1104. After a set duration, the microcontroller 908 automatically initiates transmitting information encoding the polarity assignment. In this scenario, the microcontroller 908 transmits the polarity settings in the absence of handshake signals from the wireless stimulation device. Because the microwave field stimulator 902 is operating in close proximity to wireless stimulation device 922, signal degradation may not be severe enough to warrant the use of handshake signals to improve quality of communication.

To transmit the polarity information, the microcontroller 908 reads the polarity assignment information from the non-volatile memory and generates a digital signal encoding the polarity information 1106. The digital signal encoding the polarity information may be converted to an analog signal, for example, by a digital-to-analog (DAC) converter 1112. The analog signal encoding the waveform may modulate a carrier signal at modulator 909 to generate a configuration portion of the transmission signal (1114). This configuration portion of the transmission signal may be amplified by the power amplifier 906 to generate the signal to be transmitted by antenna 907 (1116). Thereafter, the configuration portion of the transmission signal is transmitted to the wireless stimulation device 922 (1118).

Once the configuration portion is transmitted to the wireless stimulation device, the microcontroller 908 initiates the stimulation portion of the transmission signal. Similar to the configuration portion, the microcontroller 908 generates a digital signal that encodes the stimulation waveform. The digital signal is converted to an analog signal using the DAC. The analog signal is then used to modulate a carrier signal at modulator 909 to generate a stimulation portion of the transmission signal.

In other implementations, the microcontroller 908 initiates the polarity assignment protocol after the microcontroller 908 has recognized a power-on reset signal transmitted by the neural stimulator. The power-on reset signal may be extracted from a feedback signal received by microcontroller 908 from the wireless stimulation device 922. The feedback signal may also be known as a handshake signal in that it alerts the microwave field stimulator 902 of the ready status of the wireless stimulation device 922. In an example, the feedback signal may be demodulated and sampled to digital domain before the power-on reset signal is extracted in the digital domain.

Figure 12:
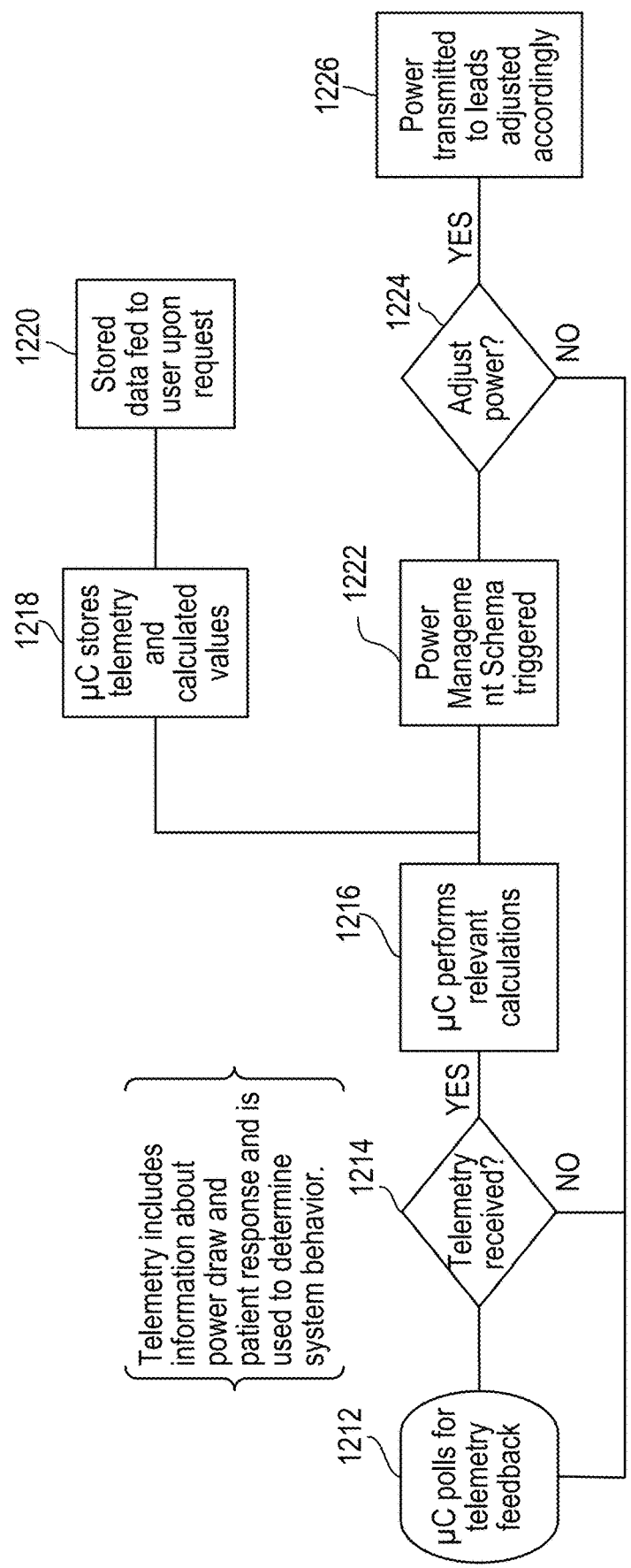
FIG. 12 is another flow chart showing an example process in which the MFS receives and processes the telemetry feedback signal to make adjustments to subsequent transmissions.

FIG. 12 is a flow chart showing an example of the process in which the microwave field stimulator 902 receives and processes the telemetry feedback signal to make adjustments to subsequent transmissions.

In some implementations, the microcontroller 908 polls the telemetry feedback module 1002 (1212). The polling is to determine whether a telemetry feedback signal has been received (1214). The telemetry feedback signal may include information based on which the MFS 902 may ascertain the power consumption being utilized by the electrodes of the wireless stimulation device 922. This information may also be used to determine the operational characteristics of the combination system of the MFS 902 and the wireless stimulation device 922, as will be discussed in further detail in association with FIG. 13. The information may also be logged by the microwave field stimulator 902 so that the response of the patient may be correlated with past treatments received over time. The correlation may reveal the patient's individual response to the treatments the patient has received up to date.

If the microcontroller 908 determines that telemetry feedback module 1002 has not yet received telemetry feedback signal, microcontroller 908 may continue polling (1212). If the microcontroller 908 determines that telemetry feedback module 1002 has received telemetry feedback signal, the microcontroller 908 may extract the information contained in the telemetry feedback signal to perform calculations (1216). The extraction may be performed by demodulating the telemetry feedback signal and sampling the demodulated signal in the digital domain. The calculations may reveal operational characteristics of the wireless stimulation device 922, including, for example, voltage or current levels associated with a particular electrode, power consumption of a particular electrode, and/or impedance of the tissue being stimulated through the electrodes.

Thereafter, in certain embodiments, the microcontroller 908 may store information extracted from the telemetry signals as well as the calculation results (1218). The stored data may be provided to a user through the programmer upon request (1220). The user may be the patient, the doctor, or representatives from the manufacturer. The data may be stored in a non-volatile memory, such as, for example, NAND flash memory or EEPROM.

In other embodiments, a power management schema may be triggered 1222 by the microcontroller (908). Under the power management schema, the microcontroller 908 may determine whether to adjust a parameter of subsequent transmissions (1224). The parameter may be amplitude or the stimulation waveform shape. In one implementation, the amplitude level may be adjusted based on a lookup table showing a relationship between the amplitude level and a corresponding power applied to the tissue through the electrodes. In one implementation, the waveform shape may be pre-distorted to compensate for a frequency response of the microwave field stimulator 902 and the wireless stimulation device 922. The parameter may also be the carrier frequency of the transmission signal. For example, the carrier frequency of the transmission signal may be modified to provide fine-tuning that improves transmission efficiency.

If an adjustment is made, the subsequently transmitted transmission signals are adjusted accordingly. If no adjustment is made, the microcontroller 908 may proceed back to polling the telemetry feedback module 1002 for telemetry feedback signal (1212).

In other implementations, instead of polling the telemetry feedback module 1002, the microcontroller 908 may wait for an interrupt request from telemetry feedback module 1002. The interrupt may be a software interrupt, for example, through an exception handler of the application program. The interrupt may also be a hardware interrupt, for example, a hardware event and handled by an exception handler of the underlying operating system.

Figure 13:
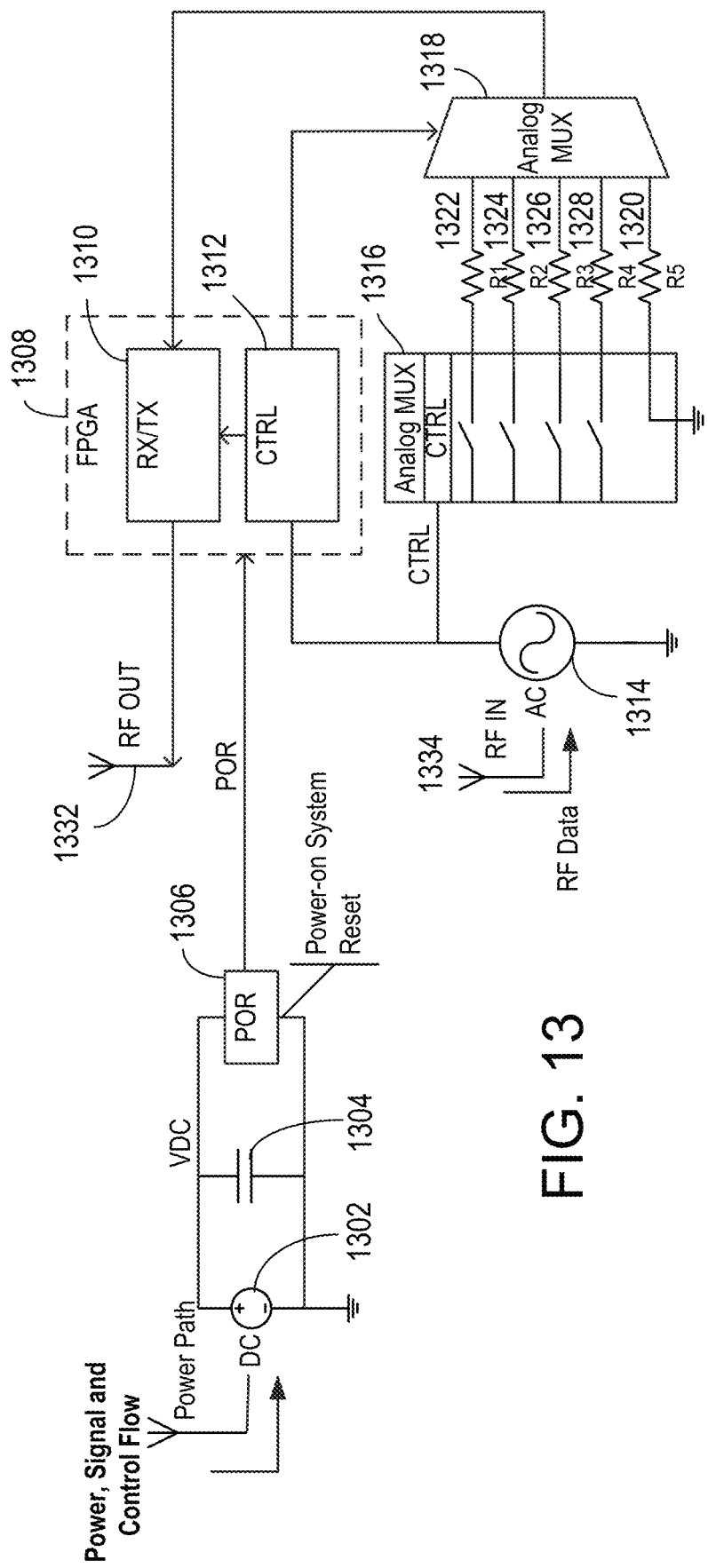
FIG. 13 is a schematic of an example implementation of power, signal and control flow on the wireless stimulation device.

FIG. 13 is a schematic of an example implementation of the power, signal and control flow for the wireless stimulation device 922. A DC source 1302 obtains energy from the transmission signal received at the wireless stimulation device 922 during the initial power-on portion of the transmission signal while the RF power is ramping up. In one implementation, a rectifier may rectify the received power-on portion to generate the DC source 1302 and a capacitor 1304 may store a charge from the rectified signal during the initial portion. When the stored charge reaches a certain voltage (for example, one sufficient or close to sufficient to power operations of the wireless stimulation device 922), the power-on reset circuit 1306 may be triggered to send a power-on reset signal to reset components of the neural stimulator. The power-on set signal may be sent to circuit 1308 to reset, for example, digital registers, digital switches, digital logic, or other digital components, such as transmit and receive logic 1310. The digital components may also be associated with a control module 1312. For example, a control module 1312 may include electrode control 252, register file 732, etc. The power-on reset may reset the digital logic so that the circuit 1308 begins operating from a known, initial state.

In some implementations, the power-on reset signal may subsequently cause the FPGA circuit 1308 to transmit a power-on reset telemetry signal back to MFS 902 to indicate that the implantable wireless stimulation device 922 is ready to receive the configuration portion of the transmission signal that contains the polarity assignment information. For example, the control module 1312 may signal the RX/TX module 1310 to send the power-on reset telemetry signal to the telemetry antenna 1332 for transmission to MFS 902.

In other implementations, the power-on reset telemetry signal may not be provided. As discussed above, due to the proximity between MFS 902 and implantable, passive neural stimulator 922, signal degradation due to propagation loss may not be severe enough to warrant implementations of handshake signals from the implantable, passive stimulator 922 in response to the transmission signal. In addition, the operational efficiency of implantable, passive neural stimulator 922 may be another factor that weighs against implementing handshake signals.

Once the FPGA circuit 1308 has been reset to an initial state, the FPGA circuit 1308 transitions to a configuration mode configured to read polarity assignments encoded on the received transmission signal during the configuration state. In some implementations, the configuration portion of the transmission signal may arrive at the wireless stimulation device through the RX antenna 1334. The transmission signal received may provide an AC source 1314. The AC source 1314 may be at the carrier frequency of the transmission signal, for example, from about 300 MHz to about 8.

Thereafter, the control module 1312 may read the polarity assignment information and set the polarity for each electrode through the analog mux control 1316 according to the polarity assignment information in the configuration portion of the received transmission signal. The electrode interface 252 may be one example of analog mux control 1316, which may provide a channel to a respective electrode of the implantable wireless stimulation device 922.

Once the polarity for each electrode is set through the analog mux control 1316, the implantable wireless stimulation device 922 is ready to receive the stimulation waveforms. Some implementations may not employ a handshake signal to indicate the wireless stimulation device 922 is ready to receive the stimulation waveforms. Rather, the transmission signal may automatically transition from the configuration portion to the stimulation portion. In other implementations, the implantable wireless stimulation device 922 may provide a handshake signal to inform the MFS 902 that implantable wireless stimulation device 922 is ready to receive the stimulation portion of the transmission signal. The handshake signal, if implemented, may be provided by RX/TX module 1310 and transmitted by telemetry antenna 1332.

In some implementations, the stimulation portion of the transmission signal may also arrive at implantable wireless stimulation device through the RX antenna 1334. The transmission signal received may provide an AC source 1314. The AC source 1314 may be at the carrier frequency of the transmission signal, for example, from about 300 MHz to about 8 GHz. The stimulation portion may be rectified and conditioned in accordance with discussions above to provide an extracted stimulation waveform. The extracted stimulation waveform may be applied to each electrode of the implantable wireless stimulation device 922. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings for the corresponding channel.

In some implementations, each channel of analog mux control 1316 is connected to a corresponding electrode and may have a reference resistor placed serially. For example, FIG. 13 shows reference resistors 1322, 1324, 1326, and 1328 in a serial connection with a matching channel. Analog mux control 1316 may additionally include a calibration resistor 1320 placed in a separate and grounded channel. The calibration resistor 1320 is in parallel with a given electrode on a particular channel. The reference resistors 1322, 1324, 1326, and 1328 as well as the calibration resistor 1320 may also be known as sensing resistors 718. These resistors may sense an electrical parameter in a given channel, as discussed below.

In some configurations, an analog controlled carrier modulator may receive a differential voltage that is used to determine the carrier frequency that should be generated. The generated carrier frequency may be proportional to the differential voltage. An example analog controlled carrier modulator is VCO 733.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 1320 and the standard voltage. One example standard voltage may be the ground.

In another configuration, the carrier frequency may reveal an impedance characteristic of a given channel. For example, the differential voltage may be the difference between the voltage at the electrode connected to the channel under measurement and a voltage across the reference resistor in series. Because of the serial connection, a comparison of the voltage across the reference resistor and the voltage at the electrode would indicate the impedance of the underlying tissue being stimulated relative to the impedance of the reference resistor. As the reference resistor's impedance is known, the impedance of the underlying tissue being stimulated may be inferred based on the resulting carrier frequency.

For example, the differential voltage may be the difference between a voltage at the calibration resistor and a voltage across the reference resistor. Because the calibration resistor is placed in parallel to a given channel, the voltage at the calibration is substantially the same as the voltage at the given channel. Because the reference resistor is in a serial connection with the given channel, the voltage at the reference resistor is a part of the voltage across the given channel. Thus, the difference between the voltage at the calibration resistor and the voltage across the reference resistor correspond to the voltage drop at the electrode. Hence, the voltage at the electrode may be inferred based on the voltage difference.

In yet another configuration, the carrier frequency may provide a reading of a current. For example, if the voltage over reference resistor 1322 has been measured, as discussed above, the current going through reference resistor and the corresponding channel may be inferred by dividing the measured voltage by the impedance of reference resistor 1322.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. The telemetry feedback signal may include a signal at the resulting carrier frequency.

The MFS 902 may determine the carrier frequency variation by demodulating at a fixed frequency and measure phase shift accumulation caused by the carrier frequency variation. Generally, a few cycles of RF waves at the resulting carrier frequency may be sufficient to resolve the underlying carrier frequency variation. The determined variation may indicate an operation characteristic of the implantable wireless stimulation device 922. The operation characteristics may include an impedance, a power, a voltage, a current, etc. The operation characteristics may be associated with an individual channel. Therefore, the sensing and carrier frequency modulation may be channel specific and applied to one channel at a given time. Consequently, the telemetry feedback signal may be time shared by the various channels of the implantable wireless stimulation device 922.

In one configuration, the analog MUX 1318 may be used by the controller module 1312 to select a particular channel in a time-sharing scheme. The sensed information for the particular channel, for example, in the form of a carrier frequency modulation, may be routed to RX/TX module 1310. Thereafter, RX/TX module 1310 transmits, through the telemetry antenna 1332, to the MFS 902, the telemetry feedback encoding the sensed information for the particular channel.

Figure 14A:
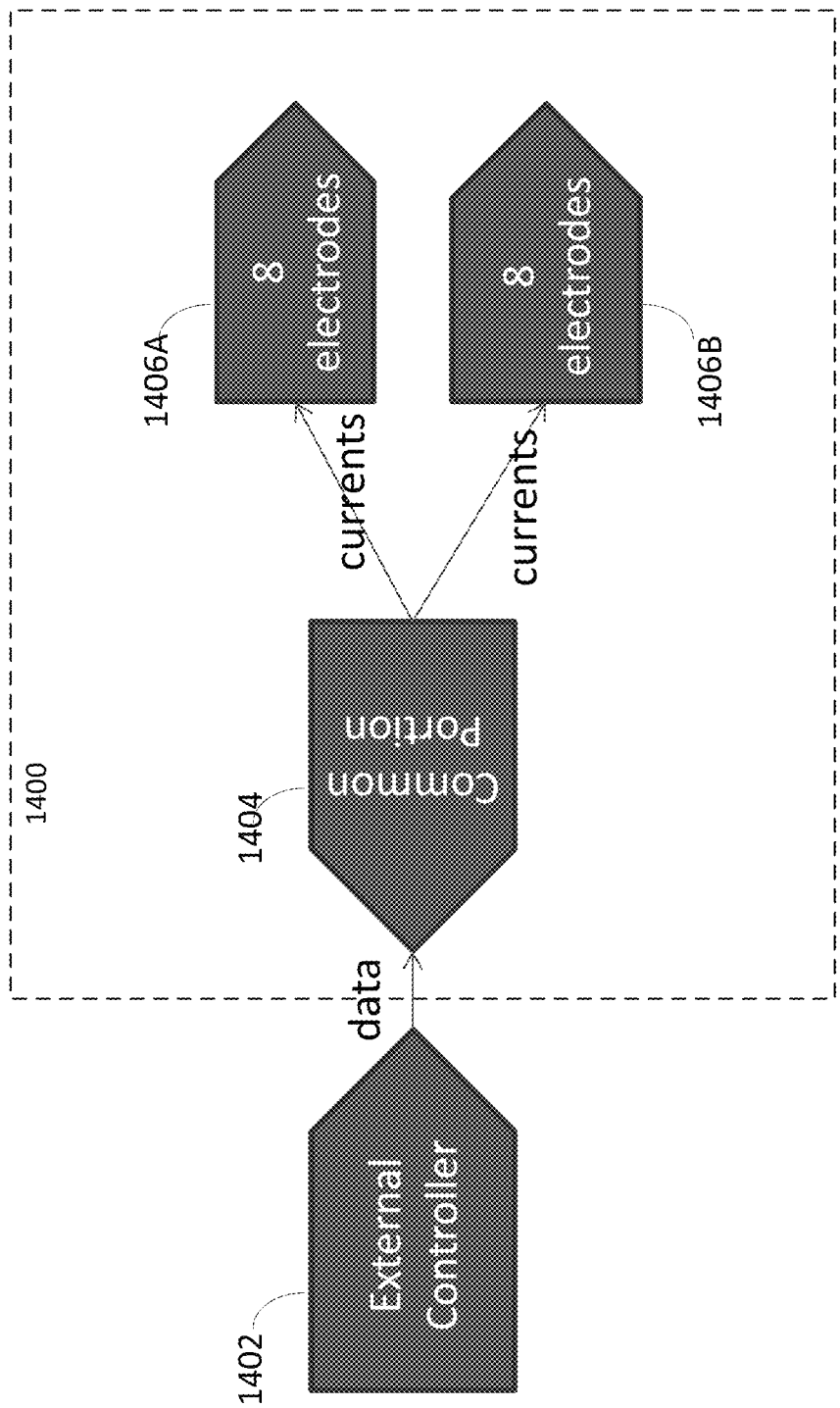
FIG. 14A is a diagram of an example of a wireless system for stimulating excitable tissue using multiple electrode arrays.

FIG. 14A is a diagram of an example of a system for stimulating an excitable tissue using multiple electrode arrays. The system includes an external controller 1402 and an implantable wireless stimulation device 1400. External controller 1402 may include a user interface and one or more antennas. In one configuration, the one or more antennas may transmit one or more input signals to the implantable device 1400 with neither cable connections nor inductive coupling. For instance, the input signals may be transmitted via electrical radiative coupling to antenna(s) on the implantable device 1400. The input signals may contain electrical energy to power the implantable device 1400. The input signals may also contain polarity assignment information for the electrodes in electrode arrays 1406A and 1406B on the implantable device 1400.

Common portion 1404 may be a central stem that houses antenna(s) for receiving the input signal as well as the circuits for harvesting the electrical energy contained in the input signal received. The circuits may also generate, using the harvested electrical energy, excitation waveforms to deliver to electrode arrays 1406A and 1406B. As illustrated, the implantable device 1400 may include two branches of electrode arrays 1406A and 1406B connected to the common portion 1404, with each array 1406A and 1406B including eight (8) electrodes. In this example, the excitation waveforms from common portion 1404 provide the current that drives each electrode on both branches.

Figure 14B:
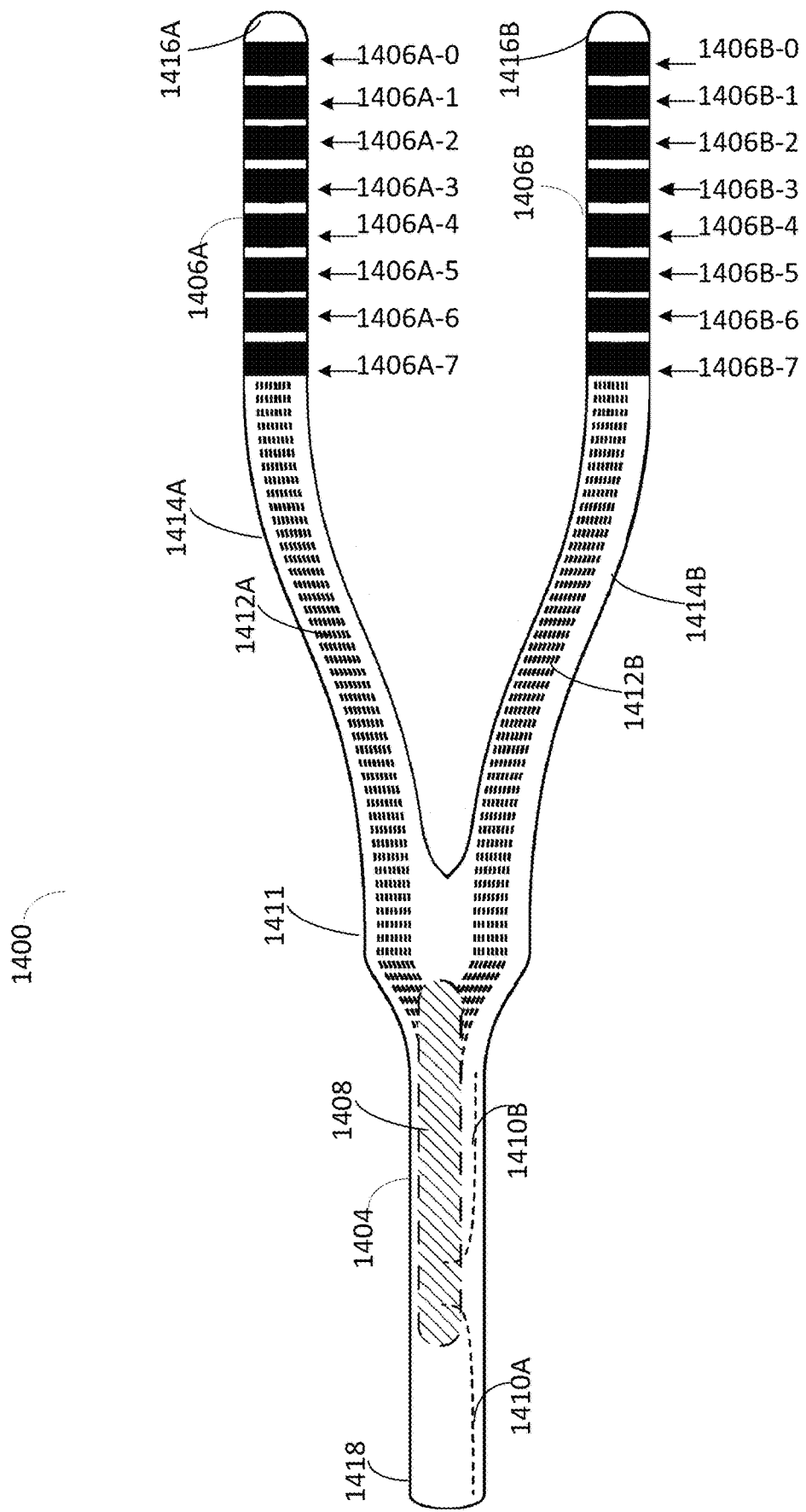
FIG. 14B is a diagram of an example of the wireless system of FIG. 14A that includes an implantable device with a Y-joint receiver with multiple connectors each integrally attached to a electrode array.

FIG. 14B is a diagram of an example of the implantable device 1400 implemented as a Y-joint receiver with two connectors integrally attached to electrode array. The implantable device 1400 includes a central stem 1404 and two branch stems 1414A and 1414B. Central stem 1404 includes a tip 1418 that may include a suturing feature for anchoring the central stem 1404 to tissue. Central stem 1404 houses antenna traces 1410A and 1410B as well as circuit 1408. In some examples, the antenna(s) on the implantable device can be positioned towards tip 1418. Antenna traces 1410A and 1410B may each be radiatively coupled to an antenna for receiving input signals from external controller 1402 and/or for sending a telemetry signal to external controller 1402. The input signal may contain electrical energy, excitation waveform parameter information, and polarity assignment information. The input signal may be received on a carrier signal having a frequency between about 800 KHz and 5.8 GHz. The electrical energy may power the entire implantable device 1400. Circuit 1408 may include waveform conditioning circuitry to extract the electrical energy from the input signal to power the implantable device. The excitation waveform may include multiple excitation pulses. The waveform parameter information may include the shape, duration, amplitude of each pulse, as well as pulse repetition frequency. The waveform conditioning circuitry may additionally create electrical pulses as stimulus pulses based on the electrical energy and according to the excitation waveform parameter information. The stimulus pulses created may be at a frequency of about 5 to 20,000 Hz. The polarity assignment information refers to the polarity assigned to each electrode on a particular electrode array. The polarity assignment may be used to program the interfaces to set the corresponding electrodes on a particular electrode array.

In the example Y-joint implantable device 1400, branch stems 1414A and 1414B respectively houses the electrode arrays 1406A and 1406B. Branch stems 1414A and 1414B may converge at fork 1411. Branch stems 1414A and 1414B may respectively include cables 1412A and 1412B, each respectively connecting circuit 1408 to the electrode arrays 1406A and 1406B. The cables may also be referred to as wires. In one example, cables 1412A and 1412B may be laser welded metal or alloy. For instance, cables 1412A and 1412B may include MP35N nickel cobalt alloy. The electrode arrays 1406A and 1406B each include eight electrodes. The electrode array 1406A includes electrodes 1406A-0 to 1406A-7. The electrode array 1406B includes electrodes 1406B-0 to 1406B-7. In one instance, each electrode may be wrapped circumferentially on the exterior wall of a branch stem. Branch stems 1414A and 1414B may extend respectively to tips 1416A and 1416B. Tips 1416A and 1416B may each include suturing features (not shown) for anchoring the respective electrode arrays to surrounding tissue.

Figure 14C:
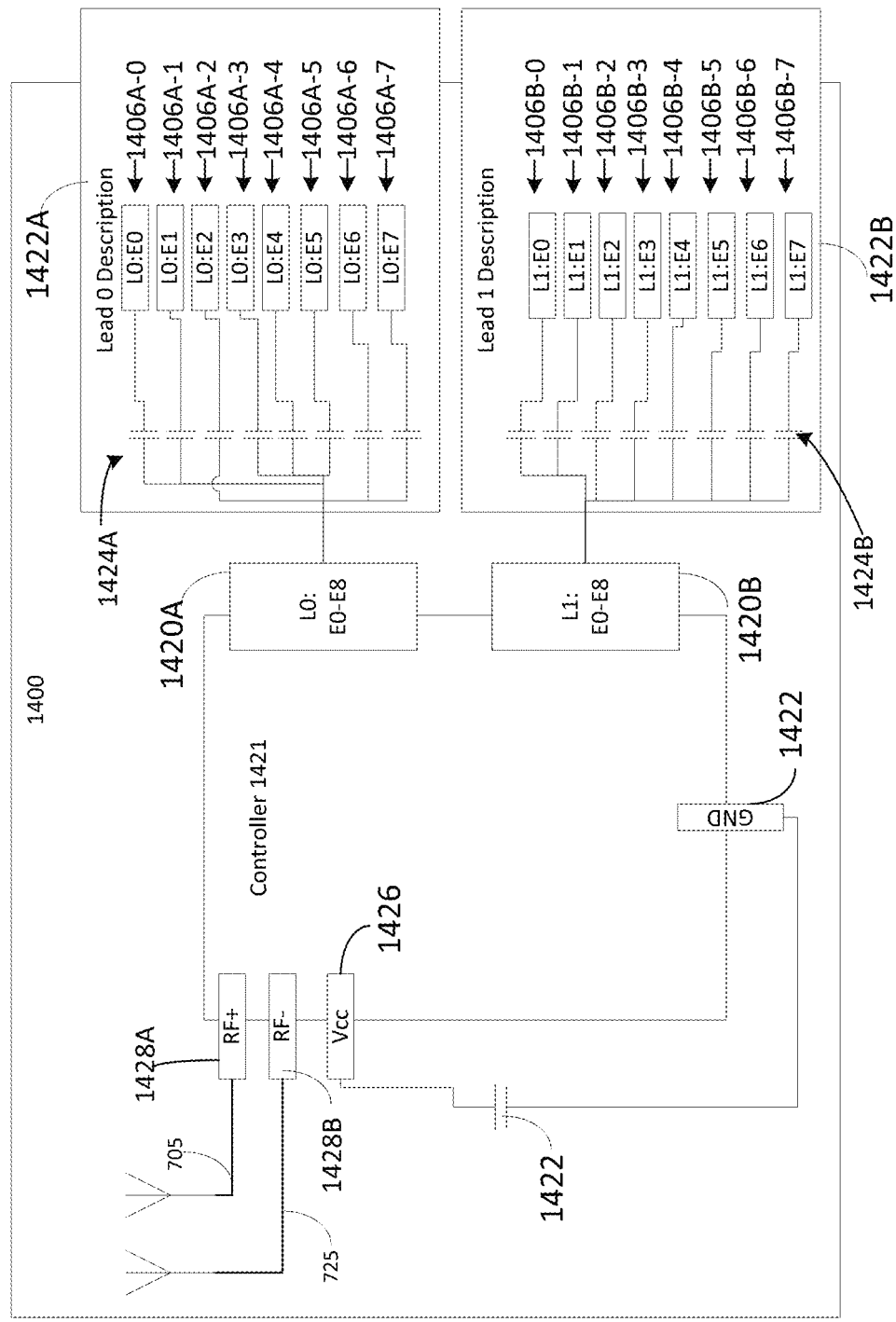
FIG. 14C is a block diagram illustrating an example of the circuitry of the implantable device with the Y-joint receiver.

FIG. 14C is a block diagram of illustrating an example of the circuitry of the implantable device 1400. An RX antenna 705 receives the input signal transmitted from external controller 1402. The input signal may be received at RX antenna 705 via electrical radiative coupling. The RX antenna 705 may be embedded as a dipole, microstrip, folded dipole or other antenna configuration other than a coil configuration. The input signal contains electrical energy for powering the wireless implantable neural stimulator 1400 and for providing stimulation pulses to electrodes 1408A0-7 and 1408B0-7. Antenna 725 may include a telemetry antenna to route received data, such as polarity assignment information, to the device interfaces 1420A and 1420B such that the polarity of electrodes on the implantable device can be programmed accordingly.

In one example, the input signal received at antenna 705 is processed at RF interface 1428A of controller 1421. Electrical energy contained in the input signal may be extracted to power the implantable neural stimulator device 1400. Stimulation pulses may be created based on the excitation waveform parameter information contained in the input signal. The created stimulus pulses can be routed to the device interfaces 1420A and 1420B to drive the respective eight electrodes connected thereto. Description box 1422A shows the schematic for electrode array 1406A. As illustrated, a capacitor bank 1424A (with eight capacitors) is available for the electrode array of eight electrodes, namely 1408A-0 to 1408A-7. A capacitor may provide power to the electrode connected thereto. Similarly, description box 1422B shows the schematic for electrode array 1406B, with capacitor bank 1424B serving the electrode array of eight electrodes, namely 1408B-0 to 1408B-7.

In another example, polarity assignment information encoded in the input signal may be received at antenna 725 and processed at RF interface 1428B of controller 1421. The polarity assignment information may be decoded and used to program the device interfaces 1420A and 1420B so that the polarities of electrodes 1408A-0 to 1408A-7 and 1408B-0 to 1408B-7 can be set according to the polarity assignment information.

Capacitor 1422 between Vcc switch 1426 and ground 1422 may store electrical energy for a power-on reset circuit. In case of a power-on event, the electric charges stored in capacitor 1422 may be used to reset the polarity assignment of each electrode and to reset register information on controller 1421.

Figure 15:
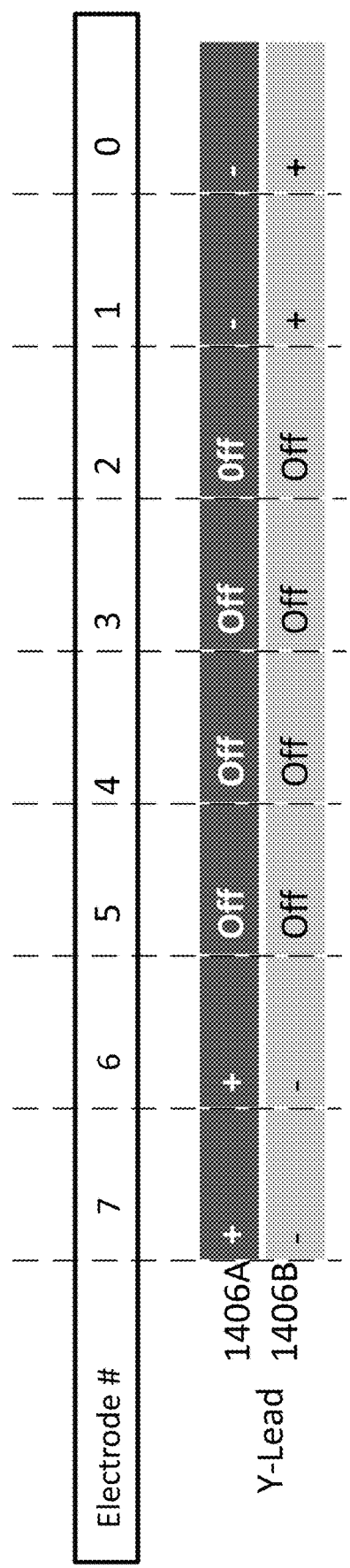
FIG. 15 shows an example of an electrode assignment for the implantable device with Y-joint receiver.

FIG. 15 shows an example of an electrode assignment for the implantable device 1400. In this example, the Y-joint implantable device includes two electrode arrays, namely, electrode array 1406A and 1406B. Each electrode array can include up to eight electrodes. However, more or less electrodes can be used for each array, or the form factor of the array may vary. As such, the array can be comprised of a cylindrical catheter type body with cylindrical electrodes spaced N distance apart, or may have a connector to a paddle or other flat, unidirectional device that contains N number of electrode pads arranged in various patterns to yield the desired effective treatment option for the stimulation of the tissue.

The electrodes on the electrode arrays 1406A and 1406B are indexed according to the top mapping in FIG. 15. In this mapping, the two electrode arrays are represented by an eight by two matrix where each row of the matrix represents one of the eight electrodes on one of the two "Y" electrode arrays. In this example, the right most electrode is mapped as electrode #0 while the left most electrode is mapped as electrode #7. The mapping in this example is linear.

The polarity assignment for a particular electrode can be cathodic (+), anodic (−), or off. Specifically, each electrode can take on a polarity of either a source or sink, known as an anode or a cathode, or otherwise denoted as positive or negative. Further, each electrode of each array can be additionally set to an on or off state, to where the circuit is functionally open and the electrode is left in a neural electrical state.

In this example, electrodes #7 and #6 of the electrode array 1406A are assigned as cathodic while electrodes #7 and #6 of the electrode array 1406B are assigned as anodic. Electrodes #3 to #5 of the electrode arrays 1406A and 1406B are assigned as off. Electrodes #1 and #2 of the electrode array 1406A are assigned as anodic while electrodes #1 and #2 of the electrode array 1406B are assigned as cathodic. The significance of programming polarity for each array on a particular electrode array will be explained in detail below.

Figure 16:
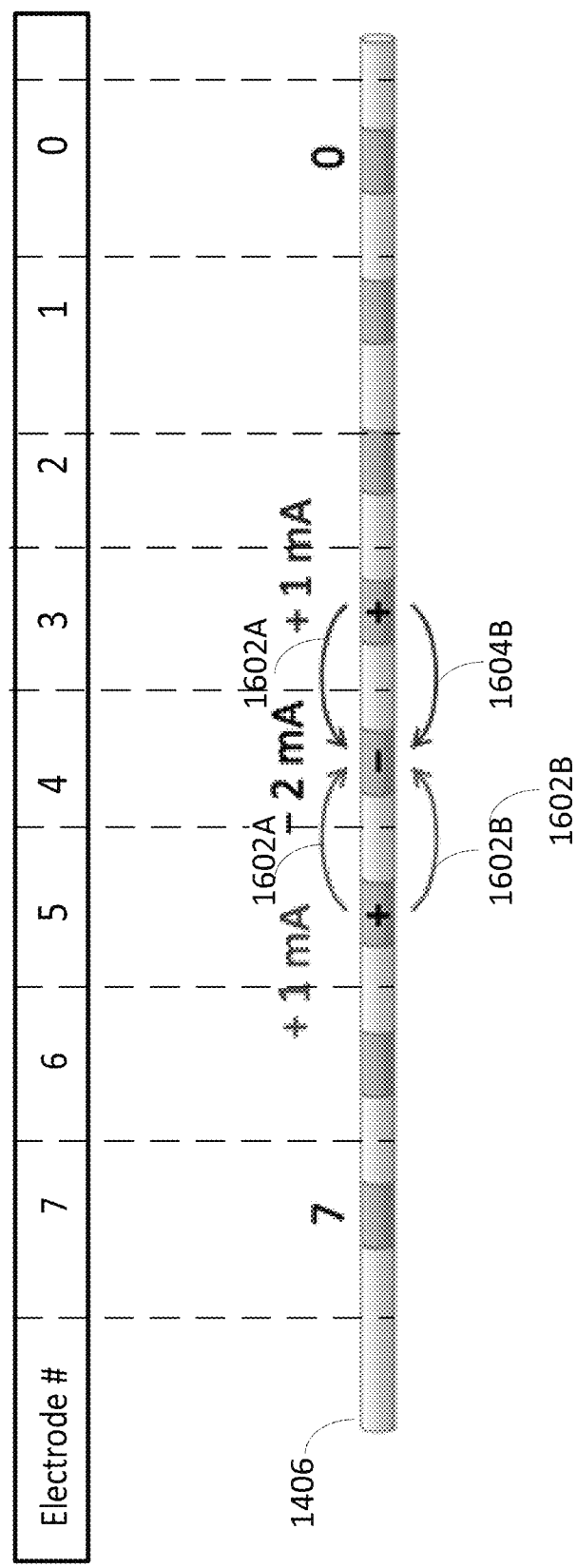
FIG. 16 shows an example of longitudinal currents formed between electrodes of a electrode array connected to the Y-joint receiver.

FIG. 16 shows an example of longitudinal currents formed between electrodes of an electrode array of the Y-joint receiver. A longitudinal current is a current that flows substantially parallel to the longitudinal axis of an electrode array. The current flows from (e.g., serving as a source) or exits at (e.g., serving as a sink) an electrode on the electrode array. In this illustration, electrodes #3 to #5 of the electrode arrays 1406A are assigned as cathodic while electrode #4 of the electrode array 1406 is assigned as anodic. As illustrated, longitudinal currents 1602A and 1602B flow from electrode #5 to electrode #4. Current 1602A is located above electrode array 1406 while current 1602B is located below electrode array 1406. When originating from electrode #5, the combined currents 1602A and 1602B may be measured at 1 mA. Longitudinal currents 1604A and 1604B may flow from electrode #2 to electrode #4. Current 1604A is located above electrode array 1406 while current 1604B is located below electrode array 1406. When originating from electrode #3, the combined currents 1602A and 1602B may be measured at 1 mA. When currents 1602A, 1602B, 1604A, and 1604B converge at electrode #4, the combined currents may be measured at 2 mA. Currents 1602A, 1602B, 1604A, and 1604B can provide therapeutic relief to excitable tissue, such as neural tissue, on their paths. This type of electrode configuration can be used to activate neural tissue lateral of the midline.

Figure 17A:
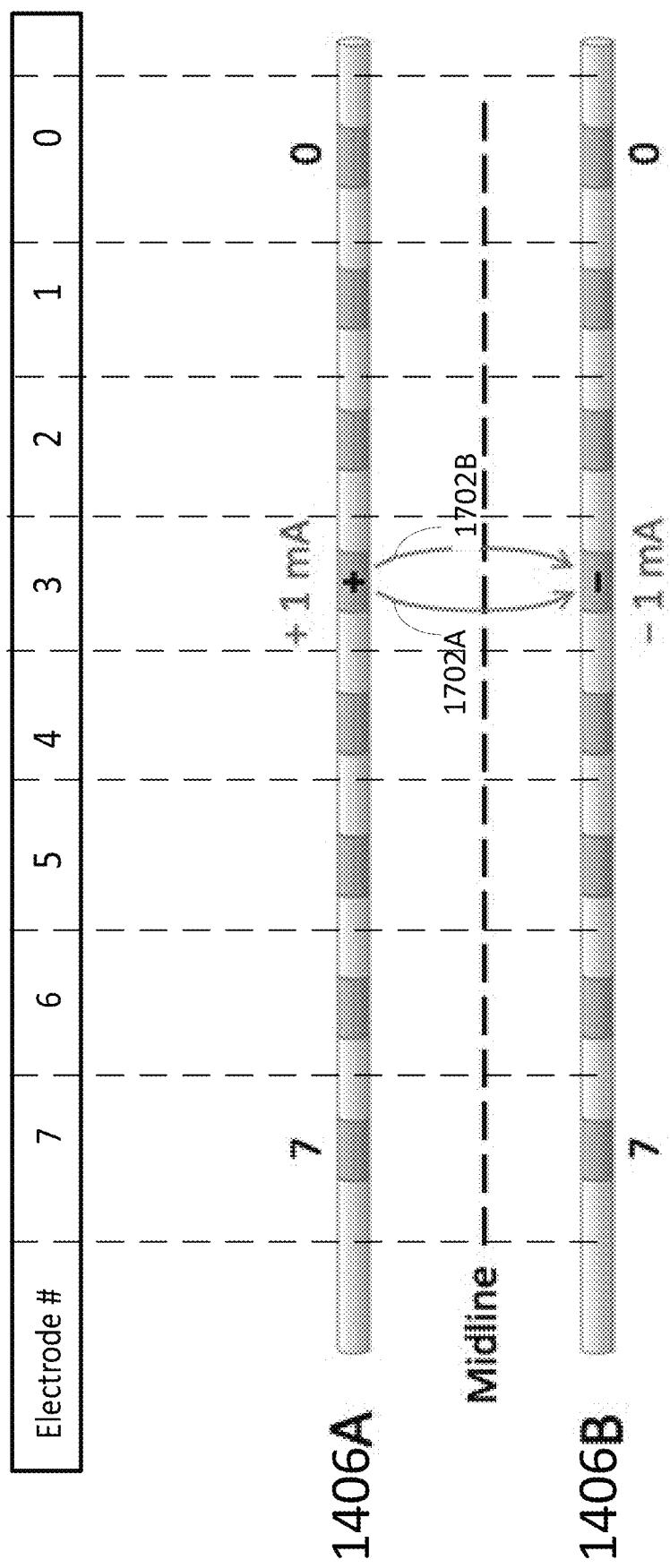
FIG. 17A shows an example of lateral currents formed between electrodes of two electrode arrays connected to the Y-joint receiver.

In some implementations, spatial distribution pattern of currents can be further enriched by the introduction of multiple electrode arrays. FIG. 17A shows an example of lateral currents formed between electrodes of two electrode arrays of the Y-joint receiver. A lateral current is a current that flows in a direction substantially transverse to a longitudinal axis of the electrode array. The current either originates from or exits at an electrode on the electrode array. In this illustration, electrode #3 of electrode array 1406A is assigned as cathodic while electrode #3 of electrode array 1406B is assigned as anodic. Currents 1702A and 1704B flow from electrode #3 of electrode array 1406A to electrode #3 of electrode array 1406B. Traversing the midline, currents 1702A and 1704B are located on mirrored paths. Originating at electrode #3 of electrode array 1406A and ending at electrode #3 on electrode array 1406B, the combined currents 1702A and 1702B are measured at 1 mA. Currents 1702A and 1704B can provide therapeutic relief to excitable tissue, such as neural tissue, on their paths. This electrode configuration can stimulate neural tissue closer to the midline with a horizontally oriented electrical field across the epidural space.

Figure 17B:
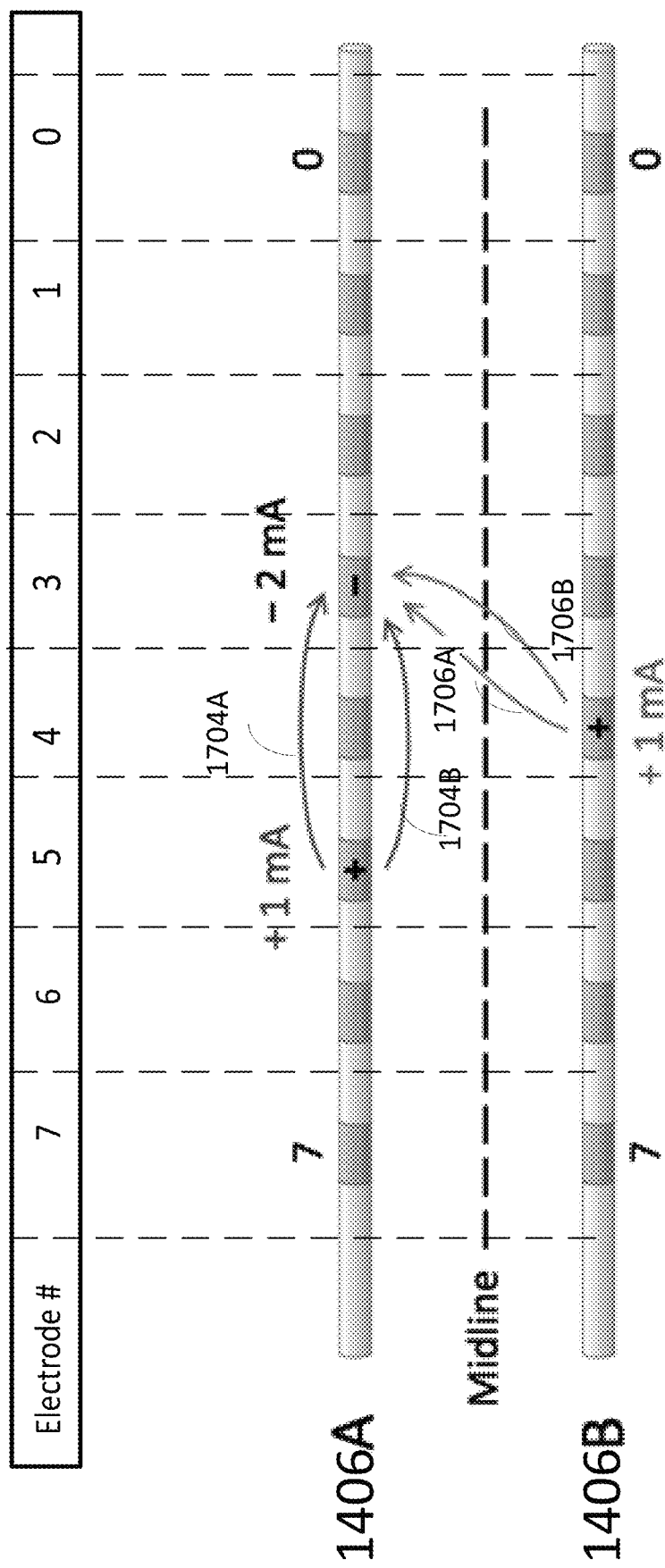
FIG. 17B shows an example of a combination of lateral current field and longitudinal current field formed between electrodes of two electrode arrays connected to a Y-joint receiver.

FIG. 17B shows an example of a combination of lateral current field and longitudinal current field formed between electrodes of two electrode arrays of a Y-joint receiver. In this illustration, electrode #3 of electrode array 1406A is assigned as anodic while electrode #5 of electrode array 1406A and electrode #4 of electrode array 1406B are assigned as cathodic. Longitudinal currents 1704A and 1704B flow from electrode #5 of electrode array 1406A to electrode #3 of electrode array 1406A. Meanwhile, lateral currents 1706A and 1706B flow from electrode #4 of electrode array 1406B to electrode #3 of electrode array 1406A. Longitudinal current 1704A is located above electrode array 1406A while longitudinal current 1704B is located below electrode array 1406A. When originating from electrode #5, the combined currents 1702A and 1702B may be measured at 1 mA. Traversing the midline, currents 1706A and 1706B are located on mirrored paths. When originating from electrode #4, the combined currents 1706A and 1706B may be measured at 1 mA. When currents 1704A, 1704B, 1706A, and 1706B converge at electrode #3 of electrode array 1406, the combined currents may be measured at 2 mA. Currents 1704A, 1704B, 1706A, and 1706B can provide therapeutic relief to excitable tissue, such as neural tissue, on their paths.

As disclosed herein, configurations of the electrodes' polarity can be set from the external controller 1402 to determine a particular electrodes combination to activate the tissue at a desired zone. In one example, the user interface on external controller 1402 to set the polarity and the power state for each electrode of the array can be in the form of a matrix interface. In this example, the matrix at the interface can be filled in by the operator for each of the N electrodes through a touchscreen. Once the matrix values are set, the operator initiates a data transfer to the central stem of the Y-joint implantable device. Circuits 1408 on board central stem 1404 may receive the data as the 8×2 matrix and store the data in self-contained memory. When electrical energy in the input signal has been harvested to power the Y-joint implant, the polarity to all those electrodes can be set according to this data in self-contained memory. In another example, the user interface on external controller 1402 may enable an operator to alter/modify the polarity setting for a particular electrode on a given array individually. In particular, the polarity setting of one electrode may be updated from the user interface on external controller 1402 without transmitting information concerning the polarity setting of other electrodes. In these examples, external controller 1402 is configured to transmit the input signal at least 12 cm, under an outer skin surface of the patient through tissue to the target site.

Figure 17C:
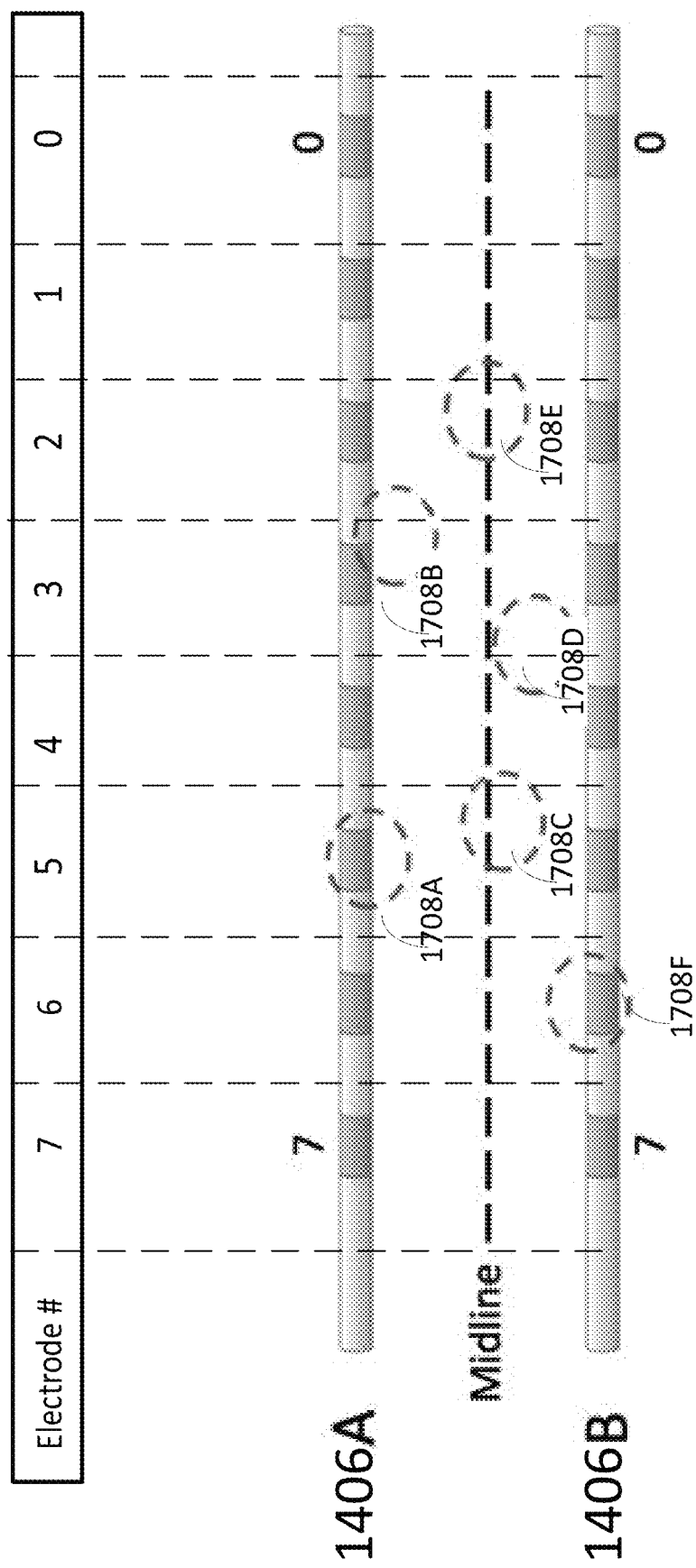
FIG. 17C shows an example of stimulation zones formed by current fields between electrodes of two electrode arrays connected to the Y-joint receiver.

FIG. 17C shows an example of stimulation zones formed by current fields between electrodes of two electrode arrays of the Y-joint receiver. Each stimulation zone is formed by virtue of electric field within the zone reaching an activation potential to cause neural activity. The electric field generated in-situ depends on electrical current as well as the impedance of the underlying tissue. The electrical current may include contributions from both longitudinal currents and lateral currents. A stimulation zone may also be known as a focal zone. Stimulation zones may be formed near an electrode, such as stimulation zones 1708A, 1708B and 1708F. Stimulation zones may also be formed away from the electrodes, for example, near mid-line, as illustrated by stimulation zones 1708C, 1708D, and 1708E.

Figure 17D:
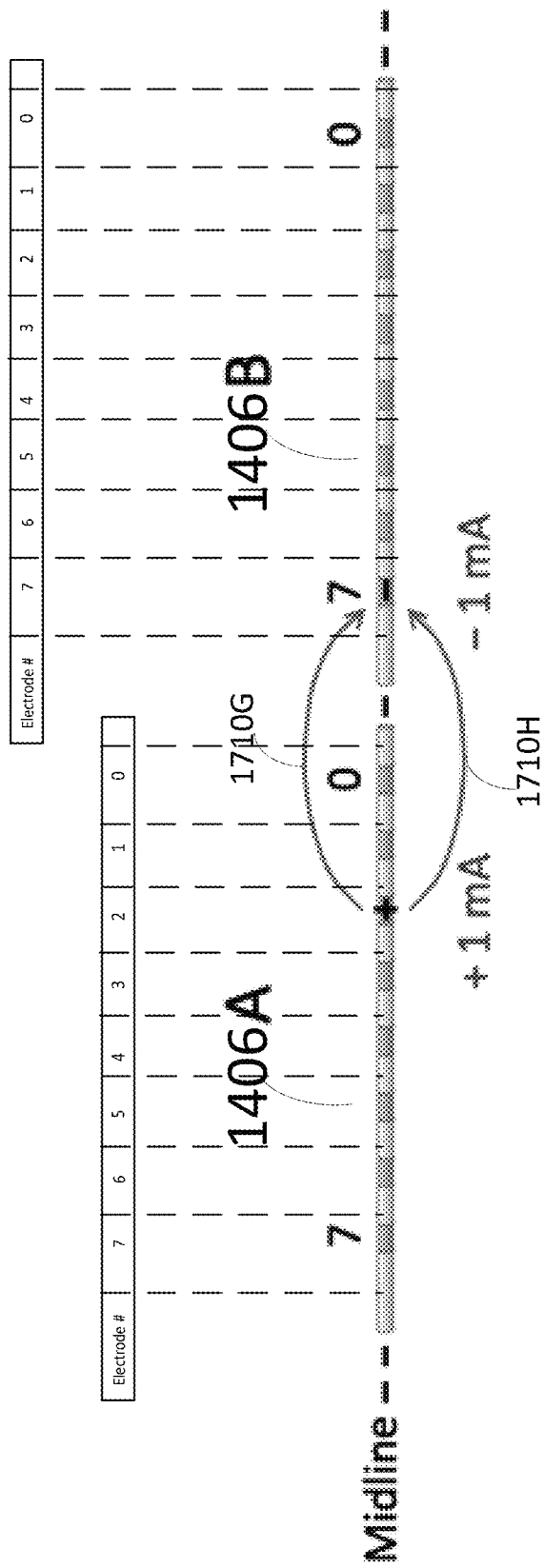
FIG. 17D shows an example of currents between two electrode arrays when the two electrode arrays are placed end to end.

A longitudinal current may also be formed between two electrode arrays, as illustrated by FIG. 17D. In this example, electrode arrays 1406A and 1406B are placed such that the distal ends are facing each other. Such placement may be achieved when the two electrode arrays form a loop, or when one electrode array is bent to tilt towards the other. In this demonstrative example, longitudinal currents 1710G and 1710H flow from electrode #2 on electrode array 1406A to electrode #7 on electrode array 1406B. Electrode #2 on electrode array 1406A is assigned as cathodic while electrode #7 on electrode array 1406B is assigned as anodic. Longitudinal current 1710G flows on top of the electrode arrays while longitudinal current 1710H flows underneath the electrode arrays. Originating at electrode #2 on electrode array 1406A, the combined strength of longitudinal currents 1710G and 1710H may be measured at 1 mA. Exiting at electrode #7 on electrode array 1406B, the combined strength of longitudinal currents 1710G and 1710H may be measured at 1 mA.

For various stimulation therapies, two or more devices may be to be placed in the epidural space where the electrodes from each electrode array can generate an electric field from one contact on one electrode array to another contact on the other electrode array. Two general scenarios may be noteworthy for placing the electrode arrays of the disclosed Y-joint implantable device. In one scenario, the electrode arrays may be placed at the same spinal level, and they are separated laterally by a few millimeters. The electrode arrays are ideally offset from the physiological midline by the same distance. FIGS. 17A to 17C correspond to this scenario. In contrast, in another scenario such as high-frequency sub-threshold stimulation, the two electrode arrays may be placed head to tail and aligned with the anatomical midline, where the combination of the two electrode arrays mimic a single long electrode array with twice the number of contacts. FIG. 17D corresponds to this latter scenario.

Figure 18A:
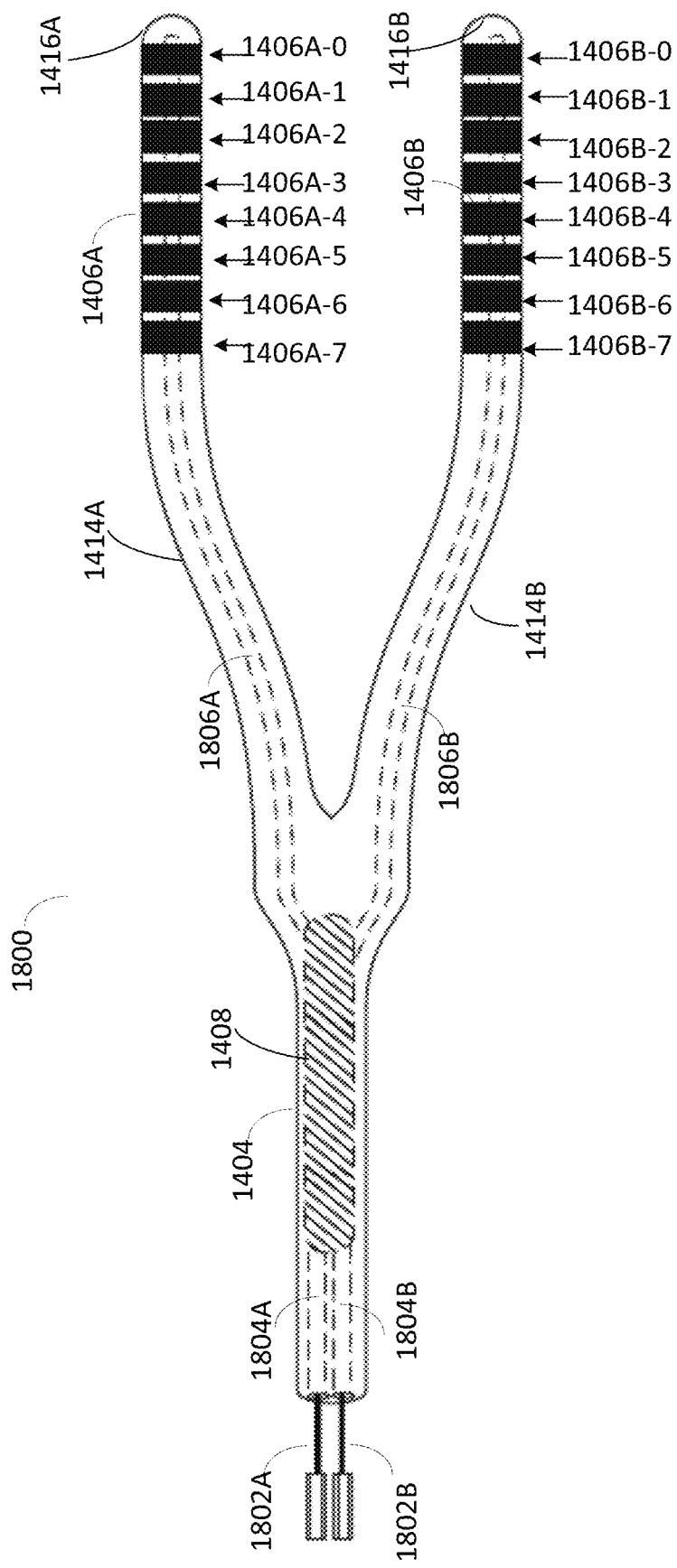
FIG. 18A shows an example of an implantable device with a Y-joint receiver in which the stylet lumen for each electrode array exits at the central stem of the Y-joint receiver.

The implantation procedure for the Y-joint receiver disclosed herein may include the use of stylets or cannulas, as discussed below. FIG. 18A shows an example of an implantable device with a Y-joint receiver in which the stylet lumen for each electrode array exits at the central stem of the Y-joint receiver. As illustrated, stylet 1802A is being placed into stylet lumen 1804A at the central stem 1404 of implantable device 1800. Stylet lumen 1804A runs through central stem 1404 which also houses circuit 1408, as discussed above. Stylet 1804A extends into branch stem 1414A and becomes stylet lumen 1806A. Stylet lumen 1806A runs through the branch stem 1414A and exits at tip 1416A. The branch stem 1414A includes electrode array 1406A with eight electrodes, namely 1406A-0 to 1406A-7, as illustrated. Likewise, stylet 1802B is being placed into stylet lumen 1804B at the central stem 1404 of implantable device 1800. Stylet lumen 1804B runs through central stem 1404 and extends into branch stem 1414B to become stylet lumen 1806B. Stylet lumen 1806B runs through the branch stem 1414B and exits at tip 1416B. This branch stem 1414B includes an electrode array 1406B with eight electrodes, namely 1406B-0 to 1406B-7, as illustrated.

Figure 18B:
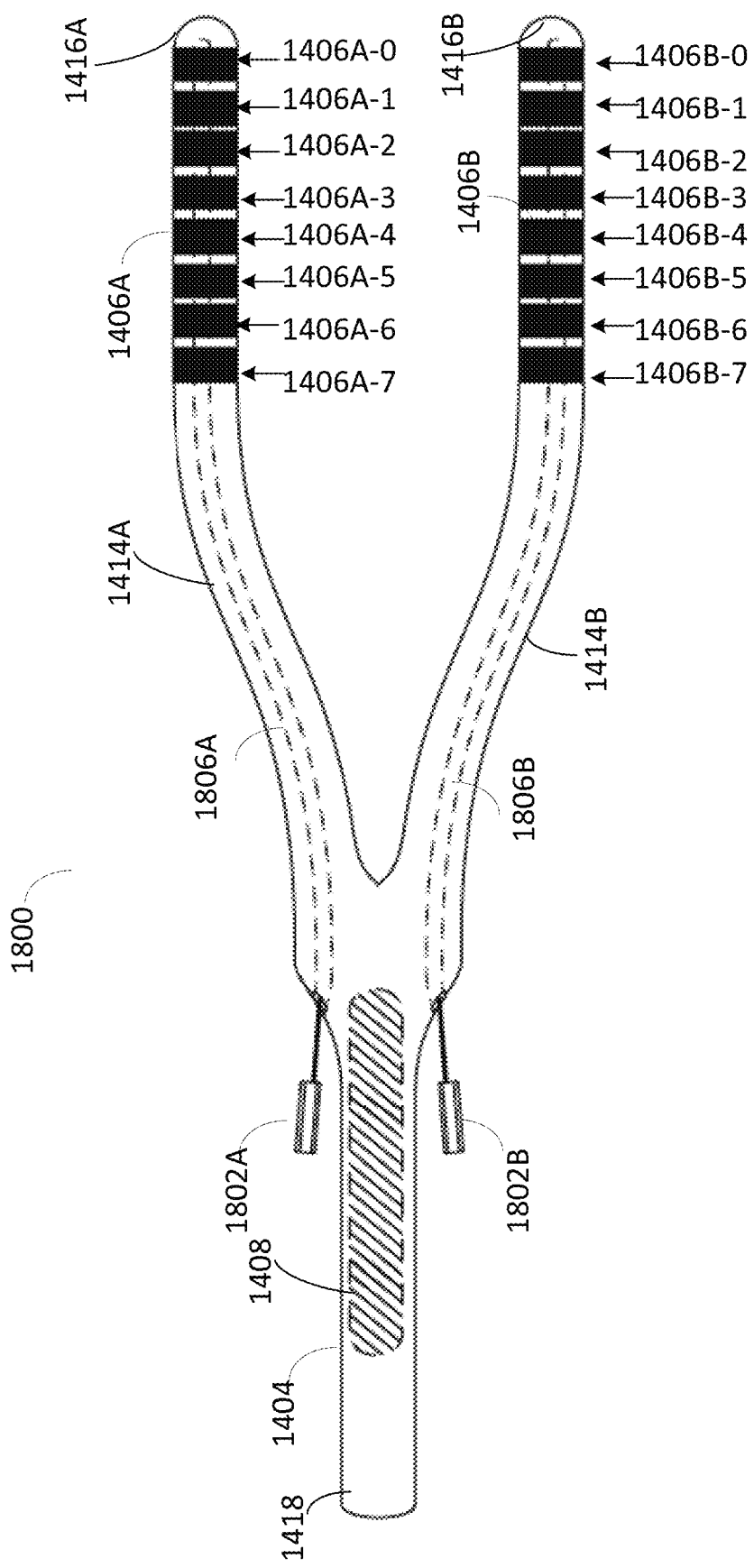
FIG. 18B shows an example of an implantable device with a Y-joint receiver in which stylet lumens for each electrode array exit at the respective stem and before the central stem of the Y-joint receiver.

FIG. 18B shows an example of an implantable device with a Y-joint receiver in which stylet lumens for each electrode array exit at the respective stem and before the central stem of the Y-joint receiver. In this example, the stylet lumens 1806A and 1806B exit the respective branch stems 1414A and 1414B before they reach central stem 1404. As illustrated, stylet 1802A is being placed into stylet lumen 1806A which runs through branch stem 1414A and exits at tip 1416A. Similarly, stylet 1802B is being placed into style lumen 1806B which runs through branch stem 1414B and exits at tip 1416B.

In the above examples, the inserted stylets may serve as guide wires to render the branch stems of the implantable device suitably rigid during implantation, such as, for example, through a needle device or an introducer device. Once an example implantable device 1800 has been placed in position, the stylets can be withdrawn from the stylet lumens. Thereafter, the implanted implantable device 1800 may be anchored to surrounding tissues, for example, by utilizing suturing features on tips 1416A, 1416B, and 1418.

Figure 19A:
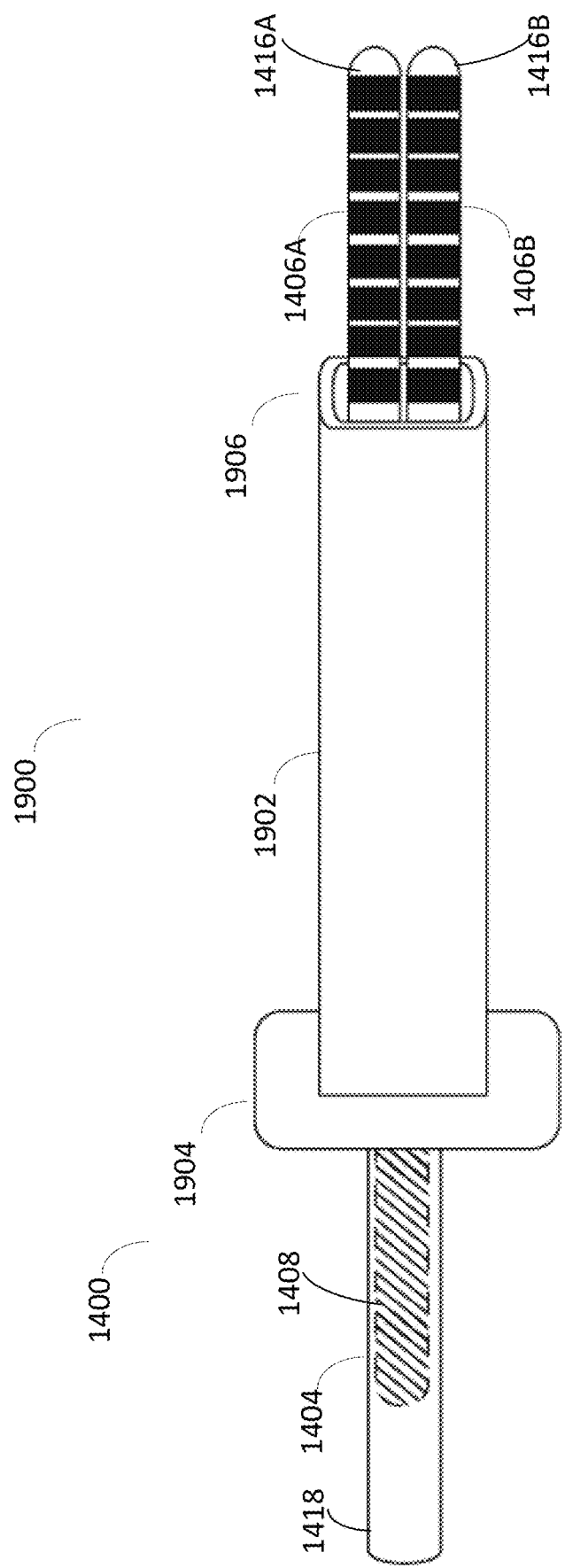
FIG. 19A shows an example of a large mouth cannula to fit both electrode arrays of an implantable device with a Y-joint receiver.

In addition to the use of stylets, cannulas may be used during implantation of the implantable device disclosed herein. FIG. 19A shows an example of a large mouth cannula to fit both the electrode arrays of an implantable device. As illustrated, branch stems houses the electrode arrays 1406A and 1406B are inserted into big mouth cannula 1900 through opening 1904 on the proximal side. The electrode arrays 1406A and 1406B may be pushed through channel 1902 and then exit big mouth cannula 1900 through opening 1906 at the distal end. Once the electrodes on the electrode arrays 1406A and 1406B have been placed in proximity of an excitable tissue, such as a neural tissue, implantable device 1400 may be anchored to the surrounding tissue. In some instances, suturing features at tips 1416A, 1416B and 1418 may be utilized during the anchoring procedure. In these instances, prior to suturing, big mouth cannula 1900 may be withdrawn from the central stem of implantable device 1400.

Figure 19B:
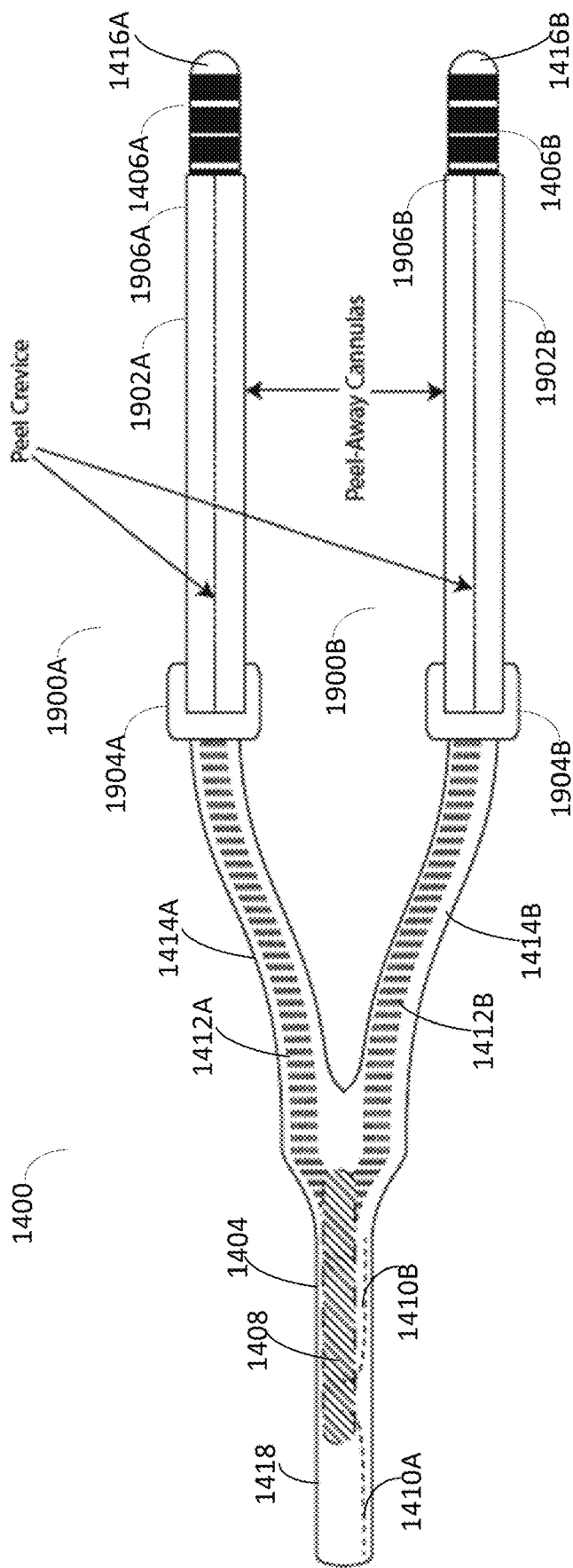
FIG. 19B shows examples of two cannulas for the electrode arrays of an implantable device with a Y-joint receiver.

FIG. 19B shows examples of two cannulas for the electrode arrays of an implantable device with a Y-joint receiver. As illustrated, branch stem 1414A houses the electrode arrays 1406A is inserted into peel-away cannula 1900A through opening 1906A on the proximal side. As disclosed herein, branch stem 1414A also houses cable 1412A that connects the electrode array 1406A to a circuit 1408 on central stem 1404. The electrode array 1406A may be pushed through channel 1902A and then exit peel-away cannula 1900A through opening 1906A at the distal end. Once the electrodes on the electrode array 1406A has been placed in proximity of an excitable tissue, such as a neutral tissue, branch stem 1414A may be anchored to the surrounding tissue. In some instances, suturing features at tip 1416A may be utilized during the anchoring procedure. In these instances, prior to suturing, peel-away cannula 1900A may be withdrawn from the branch stem 1414A of implantable device 1400. In one instance, peel-away cannula 1900A may be torn apart and stripped off branch stem 1414A.

Likewise, branch stem 1414B houses the electrode arrays 1406B which may be inserted into peel-away cannula 1900B through opening 1906B on the proximal side. Branch stem 1414B also houses cable 1412B that connects the electrode array 1406B to circuit 1408 on central stem 1404. The electrode array 1406B may be pushed through channel 1902B to exit peel-away cannula 1900A via opening 1906B at the distal end. Once the electrodes on the electrode array 1406B have been placed in proximity of an excitable tissue, such as a neutral tissue, branch stem 1414B may be anchored to the surrounding tissue. In some instances, suturing features at tip 1416B may be utilized during the anchoring procedure. In these instances, prior to suturing, peel-away cannula 1900B may be withdrawn from the branch stem 1414B of implantable device 1400. In one instance, peel-away cannula 1900B may be torn apart and stripped off branch stem 1414B for the electrode arrays of an example implantable device according to some implementations.

While using the example peel-way cannulas for an implantation procedure, the peel-away action may be subsequent to both branch stems being placed into proximity of the excitable tissue. In a similar vein, anchoring may take place when both branch stems have been stripped off the peel-away cannulas. In these instances, suturing features on tips 1416A, 1416B, and 1418 can be utilized for anchoring implantable device 1400 to surrounding tissues.

A number of implementations have been described. Nevertheless, it will be understood that various modifications may be made. Accordingly, other implementations are within the scope of the following claims.

What is claimed is:

1. A method to stimulate excitable tissue of a patient, the method comprising: implanting, using an assistive device, two or more electrode arrays of an implantable device of a stimulation system adjacent the excitable tissue of the patient without inserting an implantable battery inside the patient, wherein the two or more electrode arrays each include at least one electrode and are:
   spaced apart from each other at two different locations of the excitable tissue,
   each configured to apply at least one electrical pulse to the excitable tissue, and
   each included in a branch and the branches are distal to a central stem where the branches converge;
withdrawing the assistive device from the patient; and
after withdrawing the assistive device, operating the stimulation system to stimulate the excitable tissue of the patient, during which operation the stimulation system is configured to:
   transmit an input signal from an exterior controller module of the stimulation system to the implantable device,
   receive the input signal at one or more antenna in the implantable device, the input signal including electrical energy; and
   create the at least one electrical pulse from the electrical energy included in the input signal such that the implantable device is wirelessly powered.

2. The method of claim 1, wherein the central stem includes the one or more antenna.

3. The method of claim 1, wherein the branches and the central stem are integrally formed.

4. The method of claim 1, wherein the input signal is received by the one or more antenna in the implantable device via non-inductive electrical radiative coupling.

5. The method of claim 1, wherein the implantable device is implanted such that the two or more electrode arrays are placed bilaterally with regard to the excitable tissue and the stimulation system is further configured to form a lateral or longitudinal electrical current in the excitable tissue between the two or more electrode arrays when the at least one electrical pulse is applied at the at least one electrode of the electrode arrays.

6. The method of claim 1, wherein the implantable device is implanted such that the two or more electrode arrays are implanted longitudinally and the stimulation system is further configured to form a longitudinal electrical current in the excitable tissue between the two or more electrode arrays when the at least one electrical pulse is applied at the at least one electrode of the electrode arrays.

7. The method of claim 1, wherein the assistive device comprises at least one stylet, and the method further comprises inserting the at least one stylet into the two or more electrode arrays of the implantable device before implanting the two or more electrode arrays.

8. The method of claim 7, wherein the inserting the at least one stylet includes inserting the at least one stylet into one or more lumens in the implantable device.

9. The method of claim 8, wherein the one or more lumens are located in the two or more electrode arrays.

10. The method of claim 1, wherein the assistive device comprises at least one cannula, and the method further comprises inserting the two or more electrode arrays of the implantable device into the at least one cannula before implanting the two or more electrode arrays.

11. A method to stimulate excitable tissue of a patient, the method comprising: implanting, using an assistive device, two or more electrode arrays of an implantable device of a stimulation system adjacent the excitable tissue of the patient without inserting an implantable battery inside the patient, wherein the two or more electrode arrays each include at least one electrode and are:
   spaced apart from each other at two different locations of the excitable tissue,
   each configured to apply at least one electrical pulse to the excitable tissue, and
   each included in a branch and the branches are distal to a central stem where the branches converge;
withdrawing the assistive device from the patient; and
after implanting the two or more electrode arrays, directing an exterior controller module of the stimulation system to transmit an input signal to the implantable device, the input signal received by one or more antenna of the implantable device such that the implantable device is wirelessly powered and used by the implantable device to create the at least one electrical pulse.

12. The method of claim 11, wherein the central stem includes the one or more antenna.

13. The method of claim 11, wherein the branches and the central stem are integrally formed.

14. The method of claim 11, wherein the input signal is received by the one or more antenna of the implantable device via non-inductive electrical radiative coupling.

15. The method of claim 11, wherein the implantable device is implanted such that the two or more electrode arrays are placed bilaterally with regard to the excitable tissue and the stimulation system is further configured to form a lateral or longitudinal electrical current in the excitable tissue between the two or more electrode arrays when the at least one electrical pulse is applied by the electrode arrays.

16. The method of claim 11, wherein the implantable device is implanted such that the two or more electrode arrays are implanted longitudinally and the stimulation system is further configured to form a longitudinal electrical current in the excitable tissue between the two or more electrode arrays when the at least one electrical pulse is applied by the electrode arrays.

17. The method of claim 11, wherein the assistive device comprises at least one stylet, and the method further comprises inserting the at least one stylet into the two or more electrode arrays of the implantable device before implanting the two or more electrode arrays.

18. The method of claim 17, wherein the inserting the at least one stylet includes inserting the at least one stylet into one or more lumens in the implantable device.

19. The method of claim 18, wherein the one or more lumens are located in the two or more electrode arrays.

20. The method of claim 11, wherein the assistive device comprises at least one cannula, and the method further comprises inserting the two or more electrode arrays of the implantable device into the at least one cannula before implanting the two or more electrode arrays.

* * * * *